United States Patent
Smith

(10) Patent No.: US 11,881,303 B2
(45) Date of Patent: Jan. 23, 2024

(54) TRACKING AND QUALITY ASSURANCE OF PATHOLOGY, RADIOLOGY AND OTHER MEDICAL OR SURGICAL PROCEDURES

(71) Applicant: Complete Consent, LLC, Savannah, GA (US)

(72) Inventor: Sidney P. Smith, Savannah, GA (US)

(73) Assignee: COMPLETE CONSENT, LLC, Savannah, GA (US)

( * ) Notice: Subject to any disclaimer, the term of this patent is extended or adjusted under 35 U.S.C. 154(b) by 0 days.

(21) Appl. No.: 16/853,638

(22) Filed: Apr. 20, 2020

(65) Prior Publication Data
US 2020/0321106 A1 Oct. 8, 2020

Related U.S. Application Data

(63) Continuation-in-part of application No. 14/188,271, filed on Feb. 24, 2014, now abandoned.

(60) Provisional application No. 61/768,612, filed on Feb. 25, 2013.

(51) Int. Cl.
*G16H 40/20* (2018.01)
(52) U.S. Cl.
CPC .................................. *G16H 40/20* (2018.01)
(58) Field of Classification Search
CPC .............. G01J 2005/0081; G06K 9/00; G06T 2207/10048; G06T 2207/30201; G06T 7/0028; H04N 7/181
See application file for complete search history.

(56) References Cited

U.S. PATENT DOCUMENTS

| 8,165,363 | B2 | 4/2012 | Soenksen et al. | |
|---|---|---|---|---|
| 8,571,286 | B2 | 10/2013 | Soenksen et al. | |
| 2004/0030584 | A1 | 2/2004 | Harris | |
| 2004/0138920 | A1 | 7/2004 | Sawanaga | |
| 2005/0091084 | A1* | 4/2005 | McGuigan | G16H 20/10 705/3 |
| 2008/0051679 | A1* | 2/2008 | Maljanian | G01G 23/3728 600/587 |
| 2012/0158633 | A1 | 6/2012 | Eder | |
| 2014/0117080 | A1* | 5/2014 | Schwarz | G06Q 10/087 235/375 |

OTHER PUBLICATIONS

Admin (Select the Appropriate Inhalation Treatment code, Published on Apr. 6, 2010).

* cited by examiner

*Primary Examiner* — Reginald R Reyes
(74) *Attorney, Agent, or Firm* — Nixon & Vanderhye, PC

(57) ABSTRACT

Medical event tracking and quality assurance systems and techniques described provide a quality assurance module that interfaces between patient information systems (e.g. Electronic Health Record systems) and lab information systems. The systems and techniques provide for tracking respective medical events such as a patient's pathology specimen etc., based on a unique medical event tracking number throughout the diagnosis and treatment associated with that specimen. The system and technique enable medical event based tracking in a manner that substantially improves medical care by facilitating "closing-the-loop" between the many medical service providers and the laboratories that may be involved in a particular diagnosis and treatment.

26 Claims, 14 Drawing Sheets

FIGURE 3

| Quality Assurance Module Coding System (16) | | | | | |
|---|---|---|---|---|---|
| ICD - 10 CODE DIAGNOSIS | | | | | |
| Procedure Recommended Code (17) | 0 0 . 0 0 | | | 0 0 . 0 0 | |
| | | Time Interval (18) | | Referral Code (19) | |
| | | 0 | | | |
| Pathology Codes | | Numerical | Interval | | |
| 1. Follow-up Examination | | 1 | Day | 1. | Surgeon |
| 2. Biopsy | | 2 | Week | 2. | Oncologist |
| 3. Excision | | 3 | Month | 3. | Radiologist |
| 4. Excision with Margins | | 4 | Year | 4. | Neurologist |
| 5. Send Specimen to Referral Pathologist | | | | 5. | Other |
| 6. Other | | | | | |
| 7. ETC | | | | | |
| Radiology Codes | | | | | |
| 1. Repeat Procedure | | | | | |
| 2. Plain Films | | | | | |
| 3. CT | | | | | |
| 4. MRI | | | | | |
| 5. Mammogram | | | | | |
| 6. Ultra sound | | | | | |
| 7. Biopsy | | | | | |
| 8. Other | | | | | |

FIGURE 9C

TRACKING AND QUALITY ASSURANCE OF PATHOLOGY, RADIOLOGY AND OTHER MEDICAL OR SURGICAL PROCEDURES

CROSS-REFERENCES TO RELATED APPLICATIONS

This application is a continuation-in-part of U.S. patent application Ser. No. 14/188,271, filed Feb. 24, 2014, which claims the benefit of U.S. Provisional Patent Application Ser. No. 61/768,612, filed Feb. 25, 2013. The entire contents of U.S. patent application Ser. No. 14/188,271 and U.S. Provisional Patent Application Ser. No. 61/768,612 are herein incorporated by reference.

STATEMENT REGARDING FEDERALLY SPONSORED RESEARCH OR DEVELOPMENT (Not Applicable)

BACKGROUND

When patients present to their physician with a possible melanoma, the physician evaluates the concerning area and performs a biopsy. The biopsy is sent to a lab which, in turn, renders a diagnosis, and the patient is contacted and treated. The biopsy diagnosis is interpreted by a physician or pathologist, who may either render a final diagnosis regarding the suspected melanoma, or make further referrals to other physicians or specialists or to additional tests. A key to successful diagnosis and/or treatment of the patient's condition is the ability to complete each of the steps in this process of referrals and testing. At present, it is estimated that a substantial percentage of diagnoses and/or treatments, are unsuccessful and also that several billion dollars are spent on malpractice claims due to incomplete steps in various treatment plans. A common cause of diagnostic error is failure to respond to medical data in an appropriate manner, often referred as to failing to "close the loop."

Medical computer systems in prevalent use today merely digitize the previous pre-digital filing systems in medical offices and hospitals. The current electronic health record (EHR) systems are designed to store medical data linked to a patient's name and date of birth, as was the case with paper charts before the digital age.

The purpose of an EHR system is to document patient care and store patient medical files. Records are saved in electronic files linked to patients' unique identifying information, such as their date of birth, social security number, unique medical record number, and/or address. Attaching the patient's unique identifying information to medical events such as a lab or pathology report enables the EHR software to file information into the patient's chart. This type of storage is identical to the method used in paper charts prior to the creation of EHR.

The technical name for these EHR files is portable document format (PDF) file. The PDF files are stored using a common EHR software language called Health Language 7 (HL7). All EHRs use HL7 software. However, the EHR vendors file the patient's medical information in the different ways, which means that EHRs cannot efficiently send files between vendors. This results in a lack of interoperability.

In EHR software currently in widespread use, the data is arranged with each patient having a unique file with sub-files for different aspects, such as, for example, labs, imaging, and pathology results, and for physicians' notes. At present, patients have access to their files through patient portals for every physician and hospital where they have received treatment. Enabling patients' access to their medical records (also referred to as "health records") via patient portals is an advancement created by EHR.

Benefits that have been achieved through creation of the EHR HL7 PDF storage software include shared and quick access to a patient's records and the automatic return of lab and imaging results. Other benefits include the ability for multiple users to use charts simultaneously, electronic prescribing, integrated physician dispensing, checking of drug-drug interactions and medication allergies, recovery of files after disasters, spell checking, and improved legibility.

While these benefits are substantial, several of the most important goals that prompted the development of EHR are not being satisfactorily achieved: interoperability, collaborative quality care, effective communication, and dynamic patient-centric medical records.

At a high level, the solution to attaining interoperability would be creating a single large electronic storage system, or health information exchange (HIE). Use of HIE would provide every patient with a single portal to which every physician and health system would send patient information. Creating HIEs has been a challenge due to resistance from EHR vendors and large heath care systems. Medical data is a commodity and competitive advantage for EHR companies. Simply sharing medical information between EHR vendors is typically not in their financial interest.

Thus, further solutions are desired for interoperability of medical record systems in order to achieve improved efficiency and accuracy of treatment.

BRIEF SUMMARY

The described embodiments relate to automated tracking and quality control for pathology, surgery, and medical treatment. The system automates the entire process and adds time metrics to improve patient safety and coordinates all involved parties.

A process and platform are described that enable physicians to communicate recommendations and referrals with time metrics accessible to all health care partners. Through point of origin scan codes for specimens integrated with the lab and the Quality Assurance Module, all parties are effectively informed of each step of the process, and safeguards are established to make sure all recommendations or referrals are completed. The process and platform may be used in all medical societies. In each field of medicine such as pathology, surgery, and radiology, etc., it is desirable to follow diagnosis, recommendations, and patients' follow up. The physician, surgeon, pathologist, and patients all need a mechanism to follow labs, specimens (including x-ray reports), or recommendations to demonstrate appropriate care is received.

Medical event tracking and quality assurance systems and techniques described provide a quality assurance module that interfaces between patient information systems (e.g. Electronic Health Record systems) lab information systems (LIS) and Radiology Picture Archiving and Communication System (PACS). The systems and techniques provide for tracking respective medical events such as a patient's pathology specimen, x-ray image etc., based on a unique medical event tracking number throughout the diagnosis and treatment associated with that specimen or image. The system and technique enable medical event based tracking in a manner that substantially improves medical care by facilitating "closing-the-loop" between the many medical service providers and the laboratories that may be involved in a particular diagnosis and treatment.

In an exemplary embodiment, a medical event tracking computer system, comprises: a memory configured to store a plurality of tracked medical event records, each tracked medical event record including a unique medical event tracking number and corresponding to a tracked medical event in relation to a patient; at least one network communication interface; and a processing system comprising at least one processor. The processing system is configured to provide, via the at least one network communication interface, a first application programming interface to a patient information system and a second application programming interface to a medical testing information system.

In response to a first type of message from the patient information system received via the first application programming interface, the processing system: (1) generates a unique medical event tracking number, (2) generates a corresponding tracked medical event record in the at least one memory, and (3) associates at least one timer with the generated tracked medical event record. An event type and/or event subtype and the associated timer of the generated tracked medical event record is set in accordance with a code included in the received first type of message. In response to a second type of message from the medical testing information system received via the second application programming interface, the processing system: (1) updates a status of the generated tracked medical event record, and (2) transmits a status message to the patient information system. The processing system also transmits one or more messages including information associated with the generated tracked medical event record to a requester.

In another example embodiment, a computer-implemented medical event tracking method comprises: providing, via at least one network communication interface, a first application programming interface to a patient information system and a second application programming interface to a medical testing information system. In response to a first type of message received from the patient information system via the first application programming interface: (1) generates a unique medical event tracking number, the method (2) generates a corresponding tracked medical event record in the at least one memory, and (3) associates at least one timer with the generated tracked medical event record, wherein an event type and/or event subtype and the associated timer of the generated tracked medical event record is set in accordance with a code included in the received first type of message. In response to a second type of message received from the medical testing information system via the second application programming interface, the method: (1) updates a status of the generated tracked medical event record, and (2) transmits a status message to the patient information system. The method also transmits one or more messages including information associated with the generated tracked medical event record to a requester.

In another example embodiment, a non-transitory computer readable storage medium storing instructions for medical event tracking is provided. The instructions, when executed by a processing system including one or more processors, causes the processing system to perform operations comprising providing, via at least one network communication interface, a first application programming interface to a patient information system and a second application programming interface to a medical testing information system.

In response to a first type of message received from the patient information system via the first application programming interface, the processing system is caused to: (1) generate a unique medical event tracking number, (2) generate a corresponding tracked medical event record in the at least one memory, and (3) associate at least one timer with the generated tracked medical event record, wherein an event type and/or event subtype and the associated timer of the generated tracked medical event record is set in accordance with a code included in the received first type of message. In response to a second type of message received from the medical testing information system via the second application programming interface, the processing system is caused to: (1) update a status of the generated tracked medical event record, and (2) transmit a status message to the patient information system. The processing system is also caused to transmit one or more messages including information associated with the generated tracked medical event record to a requester.

BRIEF DESCRIPTION OF THE DRAWINGS

These and other aspects and advantages will be described in detail with reference to the accompanying drawings, in which:

FIG. 3 is a Quality Assurance Module Coding System, according to some embodiments;

FIG. 9B and FIG. 9C show example living portable document format documents, according to some embodiments;

DETAILED DESCRIPTION

Figure 1:
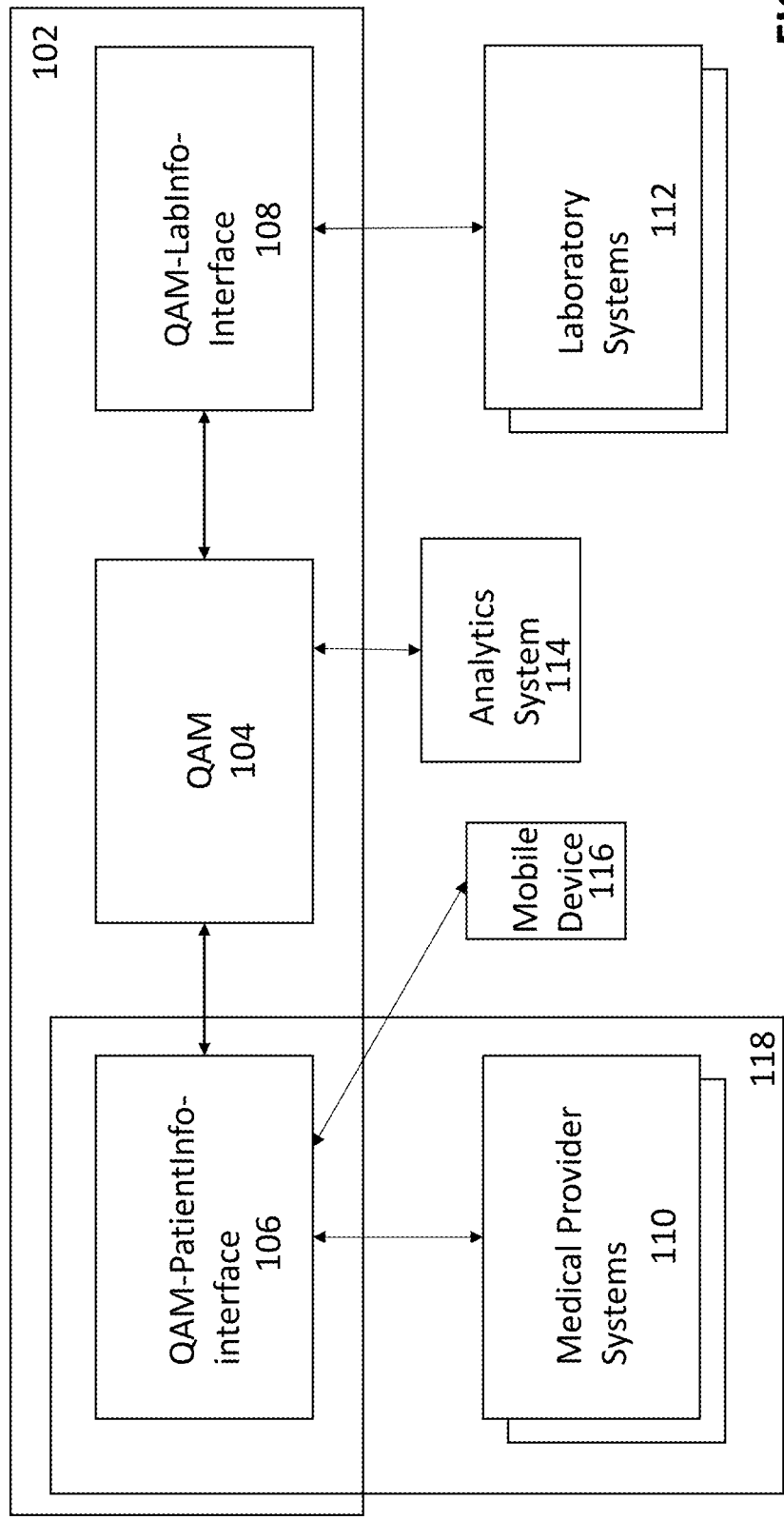
FIG. 1 is an illustration of an environment in which medical service provide computer system and laboratory information systems are interconnected by a quality assurance system.

To meet medicine's full potential, in terms of patient safety, quality, and efficiency, medical data must be tracked differently from how it is done at present. Rather than tracking a patient with a medical event, such as, for example, a biopsy or imaging report, embodiments described in this disclosure adopt an EHR communication system that tracks a medical event and links the event to the patient, a process referred to herein as medical event tracking (MET).

A chain-of-custody approach, such as that used in the package delivery industry, is adapted and employed in the tracking of trackable medical events such as, for example, biopsy specimens, clinical pathology reports, and radiology reports. However, rather than simply tracking a physical object, the medical event tracking number in embodiments can link all associated communication and documentation between care providers, laboratory personnel, and the patient. Alerts, notes, and patient communication are incorporated into this solution, in some embodiments, to effectively close the treatment loop.

MET assigns a unique medical event tracking number to each trackable medical event (also referred to as "tracked medical event"), which creates a digital space for the care continuum to interact, sharing information, quality metrics outcomes, and common medical data storage. MET can also enable direct patient engagement. Linking tracking numbers for each patient's care team interaction creates a linked care continuum involving the patient and all the care providers relevant to the tracked event.

Unique to MET is the concept of medical data life cycles (MDLC). Each medical event has a definable life span. For example, a benign skin biopsy has a relatively short MDLC and associated event documentation. The associated event data includes tracking the physical location of the specimen to the lab, communication of the report to the physician, and notification of the patient of the benign diagnosis.

In contrast, a skin biopsy demonstrating a melanoma has a MDLC that lasts the lifetime of the patient. This event data would include the same initial linked data as the benign biopsy but would also include tracking numbers for special stains, genetic studies, pharmacological treatments, and future skin examinations. The initial tracking number serves as the reference key to which all subsequent linked events are digitally attached.

An additional key step in the MET process according to some embodiments enables a physician to recommend future events, communicate instructions to the care team, and create time metrics to make sure care is delivered in a timely manner. For example, when a diagnosis of melanoma is made, the pathologist links a recommendation of excision by attaching a code to the tracking number.

This recommendation code may link a series of time metrics for calling the patient, scheduling the excision, and finally excising the melanoma. The entire care team, including the pathologist, physician, and patient, is notified if the appropriate steps are not taken in a specific timeframe. The ability of an individual physician to link future events with quality controls in this way has not existed in medicine before MET. Using MET with pathology reports means that the system may operate with no specimen being lost, every pathology report being received by the physician, every patient being notified of key events in the diagnosis and treatment, every cancer being treated, and future care being accurately coordinated.

Another key advance with MET is the creation of a "living PDF file," which eliminates "chart flipping" or the need to move from a pathology report to another section of the chart to determine if a patient received treatment. Through embedded tracking numbers in PDF pathology reports, future linked medical events are retrospectively added to linked PDF files. By simply hovering over the pathology report, care providers can see the full sequence of events linked to the report. Event information updates are sent "back-in-time" to prior reports so that any pathology report describes all subsequent related future events.

The MET platform may provide a software between the EHR and the lab information software (LIS) or Radiology Picture Archiving and Communication Systems (PACS), and application program interfaces (API) to interface with the EHR and the LIS. Using this software bridge between the EHR and LIS or PACS, the MET software creates a unique medical event tracking number shared by the practice, pathologist, radiologist, patient, currier, medical malpractice company, and insurance company. Utilizing the EHR computerized physician order entry (CPOE) system for ordering a biopsy, image (e.g. x-ray) study or the tracking platform creates the unique tracking number and a radiofrequency identification device label (RFID), which is affixed to the specimen bottle. The patient (using an application), the physician, the pathologist and the radiologist are simultaneously linked to the entire data life cycle of the event. Every stakeholder tracks the physical location of the specimen from the office to the lab with all parties receiving real-time notifications about all specimen location transitions.

The MET, according to some embodiments, may be used to coordinate the entire care team interaction, integrate genetic testing, integrate pharmaceutical therapy, track patient outcomes, integrate patient mobile devices, and enable expanded research.

Adoption of integrated MET across the care continuum addresses care interoperability issues, creates shared quality metrics, addresses communication deficiencies, and creates a dynamic patient-centric medical record. Utilizing MET, all data, recommendations, and quality metrics pass through the patient's platform, which creates a dynamic patient-centric medical record. Because MET allows any EHR platforms to integrate and enables shared, harmonizing data configurations, it provides passive data integration that creates the continuity of care record.

Creating a shared taxonomy for assessing data quality addresses the five dimensions of EHR data quality: completeness, correctness, concordance, currently, and plausibility. These features allow high quality data to be stored and presented in a manner that is usable, providing reliable, accurate, and actionable information. This approach may eliminate the highly variable correctness and completeness results observed with current HL7 EHR software.

The MET may standardize quality metrics, eliminate inconsistency across data elements, provide real-time information and communication, allow data segmentation, track completed tasks, store information prospectively, integrate data retrospectively through embedded PDF tracking numbers, and unify the data storage between the care partners. The system generates clinical quality measures though defined data life-cycle communication and performance metrics of the care team, thus documenting care transitions and outcomes.

Additionally, MET allows medical practices and communities to accurately measure performance, identify care delivery and workflow issues, and make needed corrections to deliver the highest quality, evidence-based care. It may also allow for efficient transition to value-based payments.

With MET technology, according to some embodiments, users and developers can create customized templates that integrate into their clinical workflows and maximize data completeness, creating an efficient structured data entry system (SDES). They can also adjust templates to physician preference based on encounter-specific variables, such as diagnosis, complaint, or other findings, to create structured data narratives.

Because MET provides unique API software insertions between systems, costly EHR upgrades are unnecessary or minimized; there is little or no additional cost for extraction software or services, system reconfiguration, or developing or purchasing reporting and analytics software. MET adoption has little impact on physician and staff workflow, thus minimizing the time and expense of staff training. In addition, little staff time is required to perform the data quality review and resolution process.

With the creation of high-quality real-time data, MET data enables the primary and secondary uses of data and supports the development of a learning health care system. Real-time data can be used to drive quality improvement, performance reporting and benchmarking, and clinical decision support; create the patient engagement digital space; foster payment reform and pay-for-performance; support health services research; and develop the next generation of patient-centric medical records that move beyond HIEs.

FIG. 1 illustrates a medical quality assurance system 102 configured for MET deployed in a network 100 interconnecting one or more patient information systems (e.g. EHR systems) 110 and one or more medical laboratory information systems (LIS) 112, according to some example embodiments. The medical quality assurance system 102 includes a quality assurance module (QAM) 104, a QAM—patient information system application programming interface (API) 106, and a QAM—laboratory information system API 108. In some embodiments, the medical quality assurance system 102 may also include a patient interface that can be accessed by a patient using, for example, a mobile device 116. In some embodiments, the medical quality assurance system 102 may also include, an analytics system 114.

The EHR systems 110 may be computer systems and/or networks deployed in physician's offices, hospitals, health insurers and/or other entity that has or require access to patient information. The systems 110 typically interfaces with the patient, initiates patient diagnoses and treatments, and stores patient information including personally identifiable data (e.g. patient name, date of birth, address, social security number, etc.) and patient's diagnoses and treatments. Typically, patient diagnoses, testing and treatments are initiated as a result of a patient's visit to a doctor's office or other facility that includes a system 110.

The LIS 112 may be deployed at respective laboratories and/or testing facilities. A system 112 typically receives a sample from a patient including an instruction and/or proposed diagnosis from a system 110, and returns the results of the requested test. As described in relation to FIG. 2, the testing is performed on a specimen that is transmitted from the physician's office/hospital to the testing facility offline from the electronic communication between the corresponding EHR system and LIS.

Figure 11:
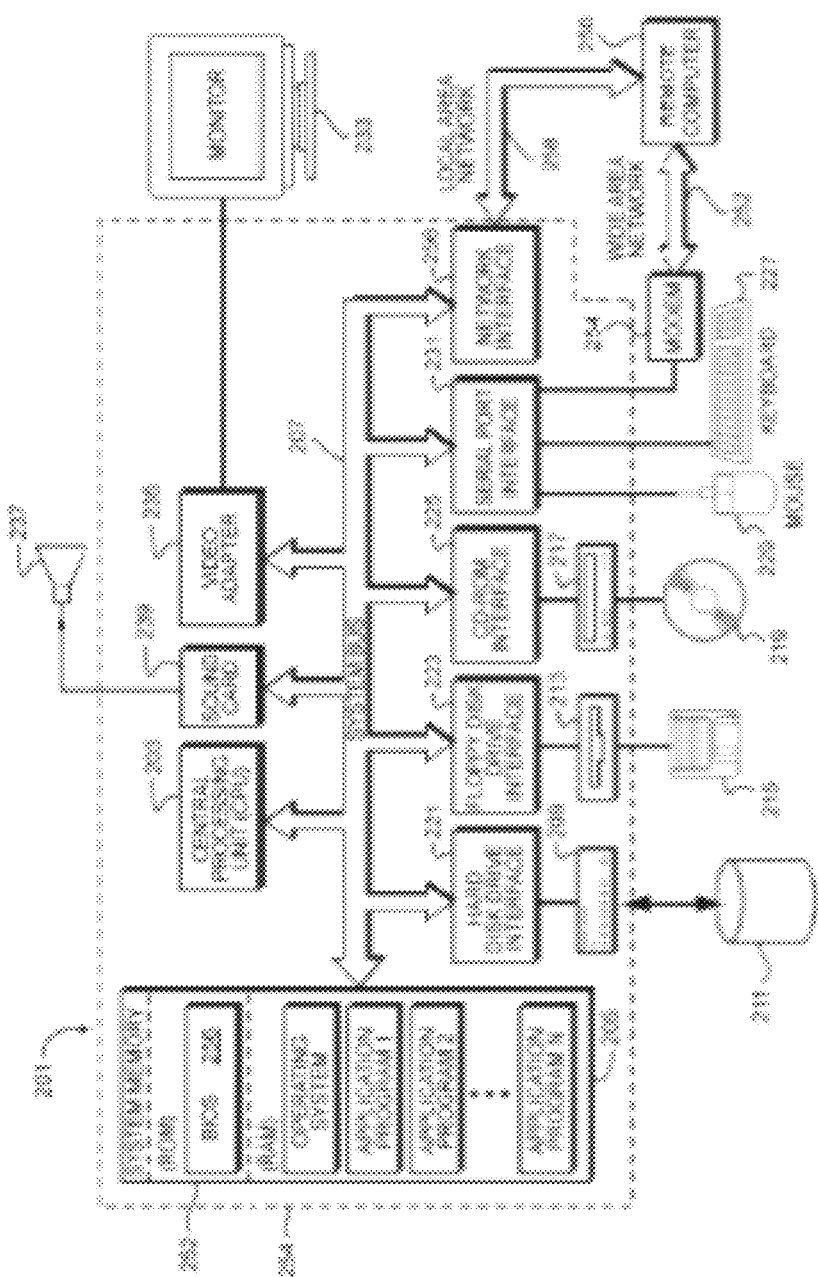
FIG. 11 is a detailed schematic of a computer system, according to some embodiments.

Each of systems 102, 110 and 112 may include one or more processing systems, such as, for example, that is described in relation to FIG. 11, and connect to one or more networks via respective network communication interfaces such that the systems 110 and 112 can communicate through system 102. At least in some embodiments, the systems 110 and 112 may be using a standardized medical environment such as, but not limited to, HL7. In some embodiments, the systems 102, 110, and 112 may be in respective network administrative domains.

The medical quality assurance system 102, according to embodiments described herein, enables communication and tracking of medical events between respective EHR systems 110, between respective LIS 112, and between EHR systems 110 and LIS 112. The communication and tracking of medical events enabled by the medical quality assurance system 102 improves efficiency of communication and coordination between the different participants in a patient's diagnosis and/or treatment, provides for "closing the loop" between the different participants in the patient's diagnosis and/or treatment, and likely reduces errors in diagnosis and treatment.

The API 106 provides for interaction between the EHR system 110 and the medical quality assurance system 102. The API 106 may also provide for the patient to interact with the medical quality assurance system 102 using a mobile device 116 or the like, for example, to display one or more screens of patient information and/or medical events associated with the patient. In some embodiments, the API 106 may maintain a mapping between the patient identifying information (e.g. one or more of patient name, date of birth, social security number) that is used to identify records in the EHR systems 110 and unique medical event tracking numbers that are used to identify records in the system 102.

The API 108 provides for interaction between the LIS 112 and the medical quality assurance system 102. The API 108 may maintain a mapping between unique medical event tracking numbers that are used to identify records in the system 102 and any tracking numbers used internally to the LIS 112. In some embodiments, however, the LIS 112 may identify its stored records using the respective unique medical event tracking numbers.

In some embodiments, analytics system 114 may provide access to the medical event records stored in the medical quality assurance system 102. With access to the records in system 102, subject to any related restrictions and regulations, the analytics system can be configured to perform analysis using the medical event records of medical events of patients from one or more EHR systems 110. In some embodiments, such analytics is facilitated, by not having any personally identifiable information of patients in the medical event records stored by the QAM 104.

In some embodiments the analytics, based on the patients of all EHR connected to the system 102 provide information about diagnosis and treatments, such as additional tests being recommended for particular health conditions. Such information can be used for predictive analytics and/or can be used in adding new or changed recommendations to treatment plans.

In some embodiments, a security domain 118 may be configured to apply to accessing any patient data stored in association with one or more of the EHR systems 110 and the API 106. The security domain 118 may ensure a higher level of security and/or authentication within the domain, that in the rest of the medical quality assurance system 102.

Figure 2:
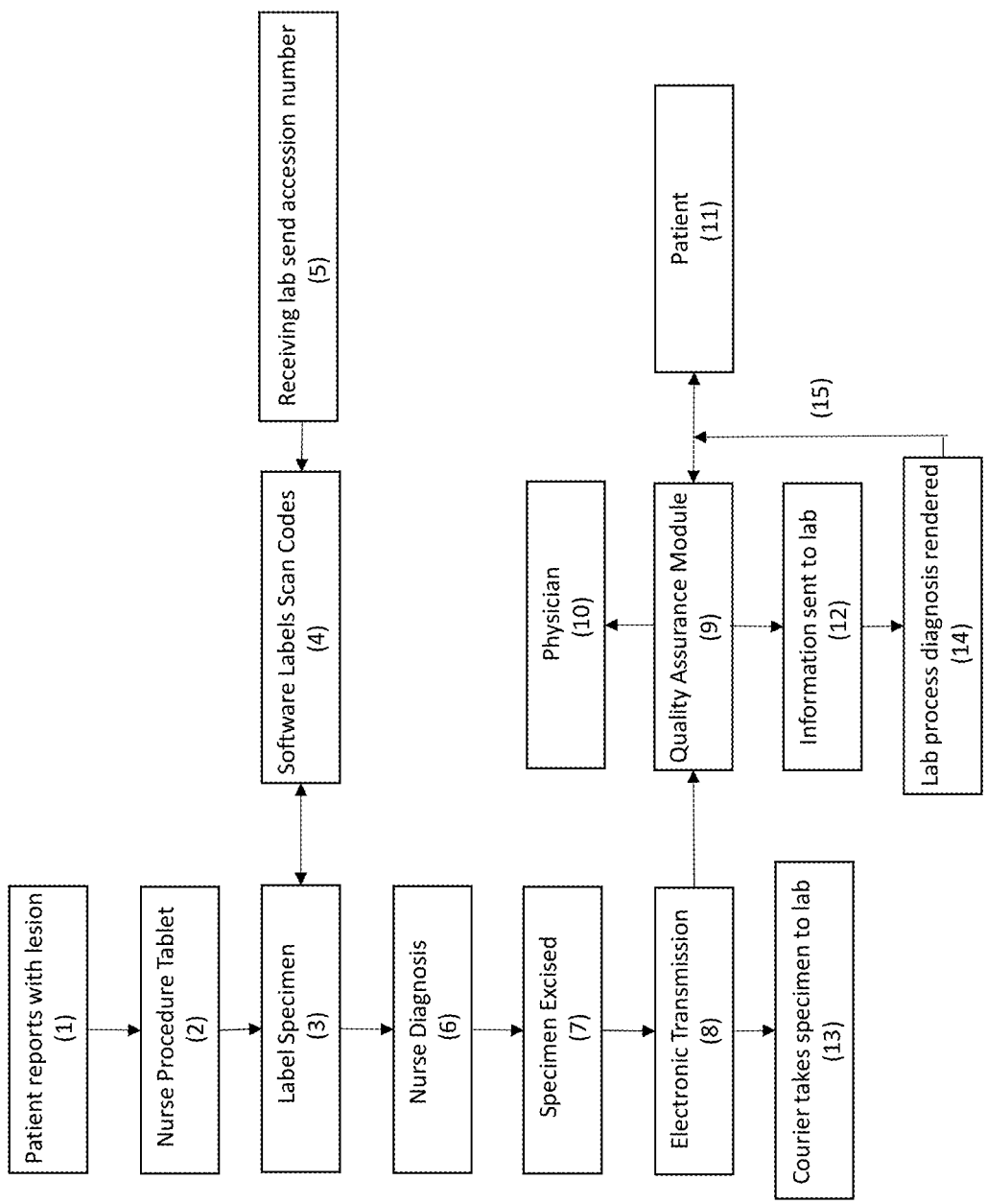
FIG. 2 is a flow diagram showing the patient visit, according to some embodiments.

With reference to FIG. 2, in the scenario of a patient presenting with a possible melanoma (1), the following protocol is followed. A nurse with a procedure tablet or the like (2) having diagrams representing the area to be removed such as a human figure, an ear, or a colon, etc. will electronically, upon touching with a pen, label the specimen as to right, left, and specifics as to the location on the body (3). Once the nurse touches the lesion diagram on the tablet, a specimen label in the form a scan code is created to place on the specimen, and simultaneously, information is sent to a computer interface that will communicate with the receiving lab (4). The information generated by the sending party includes the patient name, date of birth, patient demographics, and the physician's specimen number, location on the body, insurance information, and the physician's differential diagnosis. The QAM send a unique tracking number that will be used to identify the specimen on arrival to the lab and be used to track the specimen at the lab (5). With the above information combined the, information is then sent to the QAM, the sending physician, the patient, and the receiving lab. The specimen is removed from the patient, and the label is affixed to the bottle (7). The specimens are placed in a sealed bag accompanied by a printed document that contains all the information generated by the sending physician and receiving lab all of which is contained on each specimen's scan code. Once the specimens are labeled with the scan codes, and the printed summary document is placed in the specimen bag, the information is sent electronically to the lab, QAM, physician, patient, and courier that specimens are ready to be delivered and processed (8). The specimen information delivered to the lab (12) is integrated with their software for processing the specimens with the accession number, information for billing, and for integrating with the QAM (9). The courier is able to use the scan codes generated to document delivery times of pickup and delivery (13). The information sent from the QAM (9) to the lab is integrated with their processing software to accession the specimen and for the pathologist to render a diagnosis (14).

The pathologist renders a diagnosis and recommendation which are sent 15 to the QAM (9) via using the Quality Assurance Module coding system (FIG. 3) (16) where the information is assessable on the Quality Assurance Module (9) Interface (FIG. 5) by the physician, pathologist, and patient. Traditionally, a pathologist renders a diagnosis and occasionally an additional recommendation would be written in the "fine print" in the pathology report. Unfortunately the "fine print" recommendations are overlooked and as not part of the formal diagnosis and are not recorded in an Electronic Health Record software system (EHR). This is a very serious defect in the current EHR systems.

There are many examples of how the "fine print" recommendations in pathology and radiology for example can have tragic outcomes for patients. If a patient has a pigmented mole removed to check if the lesion is a melanoma, the pathologist may only see a portion of the entire lesion, which under the microscope is benign or non-cancerous. The pathologist may note that the mole extends beyond what he can see and is worried that the part "next door" or not removed may be the melanoma. Surprisingly, the only diagnosis codes (ICD-10) Medicare has approved for the pathologist to use is Cancer or Benign. There are no codes that allow a pathologist to diagnose with recommend additional testing. Additionally, there is no communication tool to effectively deliver "fine print" or additional recommendations from pathologist to the referring physician or patients. In the melanoma scenario employing the software, the pathologist has unique codes to access that allows him or her to communicate that the mole examined is "Benign or non-cancerous" but he recommends additional excision, biopsy, or additional examination of the patient.

Radiologists face this issue every day with every test they perform. The mammogram is a tragic example of how this can have a fatal outcome for a patient. The radiologist may examine a mammogram which is normal but a small area may be of concern but not enough to diagnose as a "cancer." The radiologist must convey a recommendation, but no codes are available to communicate with the ordering physician or patient that additional testing is necessary and at what interval.

The system has a unique set of codes selected by the pathologist, radiologist, or that are sent with the diagnosis defining any other specialist that are combined with the diagnosis codes to define additional recommendations (FIG. 3) (16). These unique codes reflect additional recommendations (17), time intervals (18), and referrals (19) for procedures needed and the time parameters for completion. In addition to the customizable codes there a group of standard QAM codes that are default metrics defined for each test (FIG. 4) (20). The additional recommendations with coding are integrated with the QAM for all parties to follow.

The basic format of the "fine print codes, or additional recommendations" is demonstrated in FIG. 3. The codes include a procedure recommendation (17) followed by a time interval (18) for completion and a referral recommendation (19) followed by a time interval (18). The procedures recommended vary by specialty such as pathology, radiology, etc. As an exemplary system, the pathologist may recommend several procedures after a biopsy such as recommending the patients have a follow up exam, biopsy, excision, excision with wide margins, or recommend sending additional specimens to a specialist (17). These codes are then combined with a numerical codes attached to a time interval line by day, week, month, or year. The pathologist for example could recommend a repeat biopsy one week from now, which as shown in FIG. 3, would be coded as 02.12/00.

The radiologist would have a similar arrangement of codes with procedures, a time interval, and referral recommendations. The radiologist may recommend a repeat procedure, plain films, CAT scan, magnetic resonance imaging, mammogram, ultrasound, biopsy (17) or other test. Additionally, a recommendation may be made for referral to another specialist such as a surgeon, oncologist, radiologist, neurologist, or other specialist (19). A radiologist may see a suspicious area on a mammogram and recommend a repeat mammogram in six months. The diagnosis would be a benign mammogram but the additional code would signify a follow-up exam, for example, 01.63/00. If the radiologist saw a lesion that needed biopsy by a surgeon within the week, another code would used, for example, 07.12/0112.12.

Each specialty would develop a standard set of codes to describe the procedures and the referral types to fully describe the specialist recommendation.

Figure 4:
FIG. 4 is a default setting for ICD-10 codes, according to some embodiments.

Specialties may establish default metric and recommendations for pathologists and radiologists to use based on the diagnosis or ICD-10 number. For example, in the scenario of the melanoma, a default setting could be that each time a diagnosis of melanoma is made, ICD-10 172.5, the system automatically adds codes recommendation of excision in three weeks, for example, 03.32/0.0. FIG. 4 demonstrates default examples of settings for a melanoma diagnosis and the recommendation of annual follow up visits and the default setting for a breast lesion recommendation of a six month follow up mammogram. In both examples, a diagnosis is made.

Figure 5:
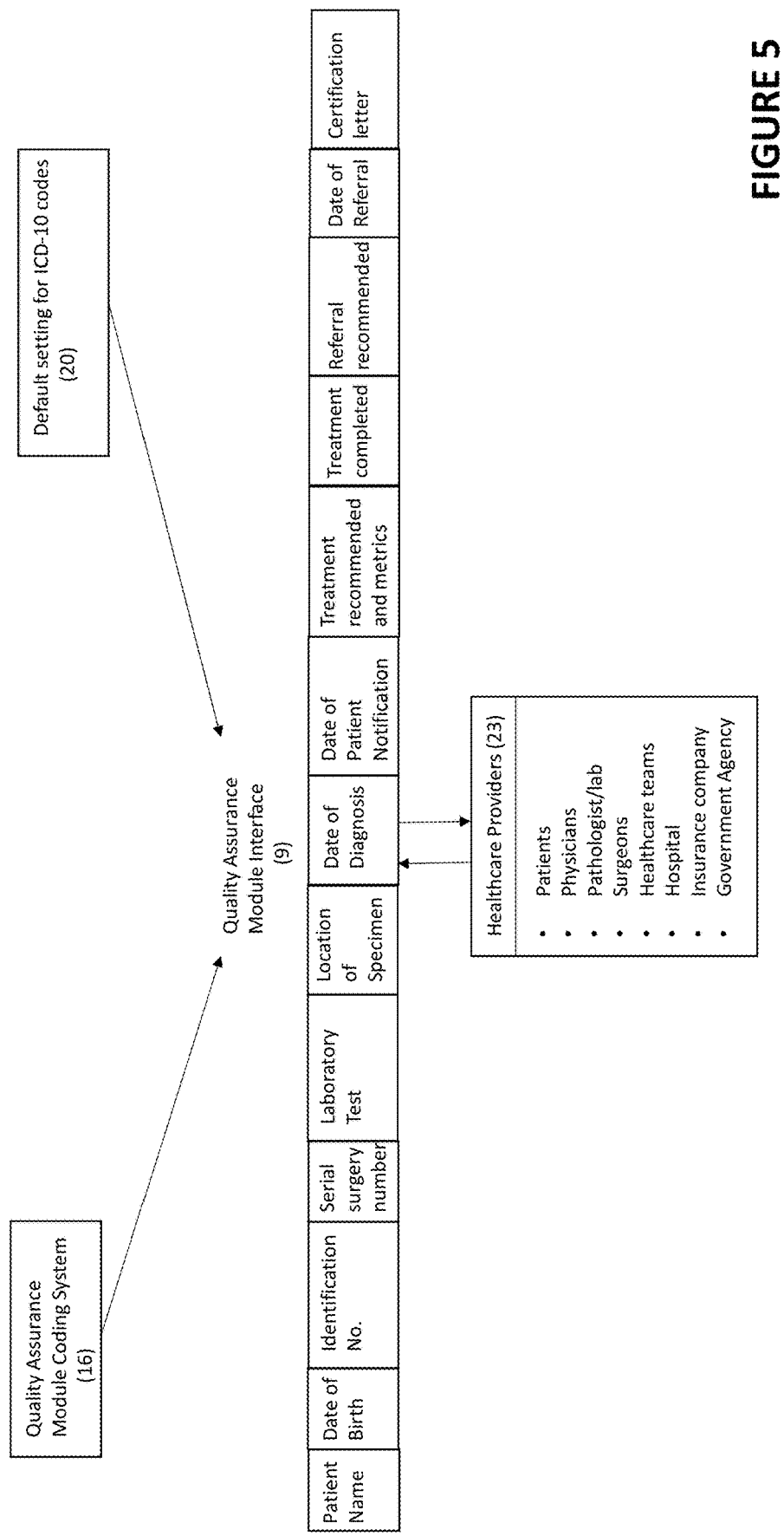
FIG. 5 is a flow diagram showing the Quality Assurance Module, according to some embodiments.

In both examples, the diagnosis ICD-10 code (21) is combined with a default setting (22) (e.g. shown in FIG. 4), and this information is sent to the QAM (9) (e.g. shown in FIG. 5).

FIG. 5 illustrates some aspects of the interface called the Quality Assurance Module (9) Interface (FIG. 4 and FIG. 5) where the healthcare providers, patients, and others (23) communicate with the QAM. Codes from the Quality Assurance Module Coding System (16) and the default settings (20) are integrated. All health providers use the same interface, and all recommendations, referrals, and time intervals can be followed.

The recommendation codes are sent to the QAM (9).

Additionally programmed with the QAM are standard time metrics specific for various diagnoses. For example, if one has melanoma, a time clock or metric is initiated allowing 10 days for the physician to contact the patient. If contact with the patient is not made, emails, text messages or other alerts are sent to the physician, and after a certain amount of time, there is a direct email sent, test message and/or other alert to the patient about the outstanding diagnosis. With reference to FIG. 5, for each step of the process, diagnosis of the specimen, notifying the physician, and notifying the patient documentation is recorded by the QAM (9) and communicated with the patient (23) (FIG. 5) and healthcare team (23) (FIG. 5). Occasionally, with some diagnoses, an additional procedure or referral may be recommended. That information is placed on the QAM with a time metric as to when the additional procedure is scheduled and what time frame the procedure should be completed with the resulting diagnosis (14) (FIG. 2). If these steps do not occur in a timely manner, the system automatically sends emails, text messages and/or other alert to the physician, the pathologist, the referral specialist and ultimately the patient. If the patient does not respond and the recommended procedure is not completed, a certified letter is generated electronically and sent to the patient closing the loop for the entire procedure.

The system notifies patients of each step their specimens take, keeping them informed along the process. Patients are notified when and where specimens are sent from the physician's office, date of arrival at the lab, date of arrival of the information at the physician's office, date of patient notification of the diagnosis, any additional recommendations or treatments, dates of future procedures, and dates of communication with certified letters. Additionally, proprietary metrics are used by the system to set the parameters for appropriate intervals in the process.

The surgical field also benefits from the QAM. A diagnosis such as a colon polyp or bronchoscopy may require scheduled follow up visits or testing. Placing these recommendations on the QAM (9) will assure compliance with the recommendations. The emergency room would benefit from a system following patient compliance for recommendations of following up with additional physicians or testing (8).

The Pathology Lab benefits by saving employee time and money not having to re-input data already recorded at the referring physician's office, having better documentation of result delivery to physicians and patients and follow up on recommendations. The referring physicians save time and money with the QAM standardized follow up, and patients benefit through continual contact which allows the process to improve communication and safety.

In the Radiology field, the process is similar to the pathology scenario. Patient demographics are transmitted with the x-ray order to the radiologist who performs the x-ray. The diagnosis rendered may require additional tests and recommendations. The additional tests or recommendations are placed by the QAM (9) with time metrics to assure they were completed. The system assures that patients receive recommended care.

The QAM may be located on the system servers in the "Cloud," accessible by the lab, physician, patient, hospital, insurance company, government agencies and other healthcare team members.

The quality assurance process described with reference to FIGS. 1-5 is preferably a browser-based system in which a program running on a user's computer (the user's web browser) requests information from a server program running on a system server. The system server sends the requested data back to the browser program, and the browser program then interprets and displays the data on the user's computer screen. The process is as follows:

1. The user runs a web browser program on his/her computer.
2. The user connects to the server computer (e.g., via the Internet). Connection to the server computer may be conditioned upon the correct entry of a password as is well known.
3. The user requests a page from the server computer. The user's browser sends a message to the server computer that includes the following:
   the transfer protocol (e.g., http://); and
   the address, or Uniform Resource Locator (URL).
4. The server computer receives the user's request and retrieves the requested page, which is composed, for example, in HTML (Hypertext Markup Language).
5. The server then transmits the requested page to the user's computer.
6. The user's browser program receives the HTML text and displays its interpretation of the requested page.

Thus, the browser program on the user's computer sends requests and receives the data needed to display the HTML page on the user's computer screen. This includes the HTML file itself plus any graphic, sound and/or video files mentioned in it. Once the data is retrieved, the browser formats the data and displays the data on the user's computer screen. Helper applications, plug-ins, and enhancements such as Java™ enable the browser, among other things, to play sound and/or display video inserted in the HTML file. The fonts installed on the user's computer and the display preferences in the browser used by the user determine how the text is formatted.

If the user has requested an action that requires running a program (e.g., a search), the server loads and runs the program. This process usually creates a custom HTML page "on the fly" that contains the results of the program's action (e.g., the search results), and then sends those results back to the browser.

Browser programs suitable for use in connection with the account management system of the described embodiments include Mozilla Firefox® and Internet Explorer available from Microsoft® Corp.

While the above description contemplates that each user has a computer running a web browser, it will be appreciated that more than one user could use a particular computer terminal or that a "kiosk" at a central location (e.g., a cafeteria, a break area, etc.) with access to the system server could be provided.

It will be recognized by those in the art that various tools are readily available to create web pages for accessing data stored on a server and that such tools may be used to develop and implement the system described below and illustrated in the accompanying drawings.

Figure 6:
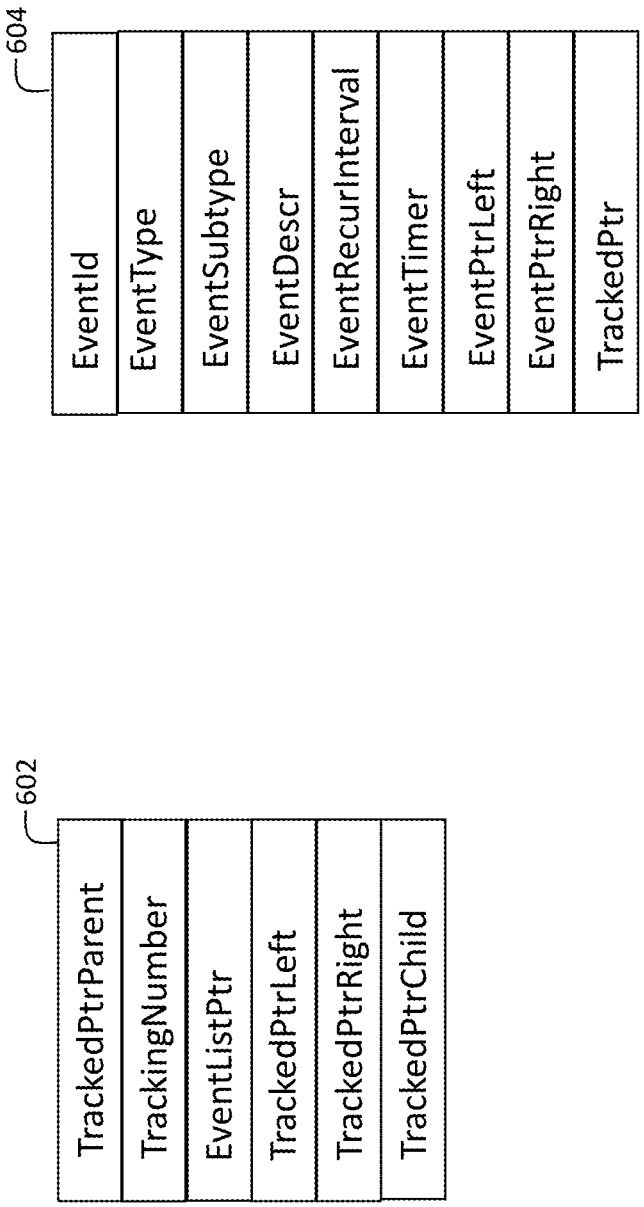
FIG. 6 illustrate an example arrangement of medical event records, according to some embodiments.

FIG. 6 illustrates example data structures for medical event records stored in the QAM, and the arrangement of related medical event records in the memory of the QAM, according to some embodiments. In the illustrated embodiments, a two-level record structure is employed for the medical event records stored and maintained in the memory of the QAM. A first type 602 of record is used to identify tracked medical events, and a second type 604 of record is used to store all other medical events stored in the QAM.

A tracked medical event is a medical event that is to be tracked by the system, and the tracking of which is used in order to improve the completion of diagnosis and treatment plans. Example tracked events include, but are not limited to, pathology specimens, image studies, any event which requires additional intervention and other lab processed information about the patient.

Each tracked event 602 causes one or more event records 604 to be created in the memory of the QAM. In one example, in the example of the melanoma diagnosis described above, a tracked event 602 is generated in the QAM for the physician taking the specimen, and a corresponding event 604 is also generated.

In the data structure 602, each tracked event includes a tracking number field ("TrackingNumber") and an event list pointer field ("EventListPtr"). The tracking number field takes a unique medical event tracking number as its value. The event pointer field's value is a pointer to an event that is represented in a data structure 604. The tracked event data structure 602 may have additional pointers, such as, for example, a pointer to a parent tracked event ("TrackedPtrParent"), a pointer to a child tracked event ("TrackedPtrChild"), a left sibling tracked event ("TrackedPtrLeft"), and a right sibling tracked event ("TrackedEventPtr Right"). This enables each tracked event to be related to other events in the memory of the QAM, in a manner that allows for high flexibility in tracking various tracked events in a diagnosis and/or treatment, and also to quickly access the tracked events related to one tracked event.

As noted above, each tracked even points to at least one event data structure 604. The event data structure 604 encodes the information about the event that enables the system to monitor the event. The event data structure 604 includes an event identifier ("EventId"), an event type ("EventType"), an event subtype ("EventSubtype"), an event description ("EventDescr"), an event recurrence interval ("EventRecurinterval"), an event timer ("EventTimer"), a pointer to the corresponding tracked event ("TrackedPtr"), a pointer to a left sibling event ("EventPtrLeft"), and a pointer to a right sibling event ("EventPtrRight").

When the QAM receives a message for a new medical event from an EHR system, the request may include ICD-10 codes as described in relation to FIGS. 3-5 specifying the recommendations (e.g. any of proposed diagnosis, specimen description, referral recommendation, follow-up time intervals, etc.) or such codes may be determined by the QAM-patient information system API based on either a predetermined translation from another set of codes specific to an EHR and/or by querying the request initiator. The ICD-10 codes or information determined based on the ICD-10 codes may be stored in the corresponding tracked event records and/or event records.

In the above described example of the melanoma specimen, when the physician submits the initial specimen to the lab, the request from the physician to the QAM causes the QAM to generated a tracked event (e.g. new instance of tracked event record 602) with a new unique medical event tracking number corresponding to the specimen submitted to the lab, and an event chain starting with an event record 604 for the physician visit. Additionally, a second event record 604 is created in accordance with a specified time interval for follow-up and a proposed diagnosis. The new tracked event record points to the first event record in the chain, which in turn points to the second event record. Each of the first and second events may point to the corresponding tracked event record. Both the first and second event records may be configured with timer values either according to system configured event type specific default values or values specifically conveyed in the request.

The QAM implements a timer mechanism to enable each event record to have its own timer value.

In some embodiments, in addition to the above described fields of the data structures 602 and 604, fields may be available in one or more of 602 or 604 to maintain relevant information such as laboratory test, location of specimen, date of diagnosis, date of patient notification, treatment recommendations and metrics, treatment completed date, referral recommended, referral completed date, etc. The QAM-Patient information system operates to, using a maintained mapping of patient identification information in the EHR to medical event tracking numbers in the QAM, dynamically assemble patient information and/or reports combining patient information from EHR and lab and/or referral information from the QAM. An example combined records or report is shown in FIG. 5.

Figure 7A:
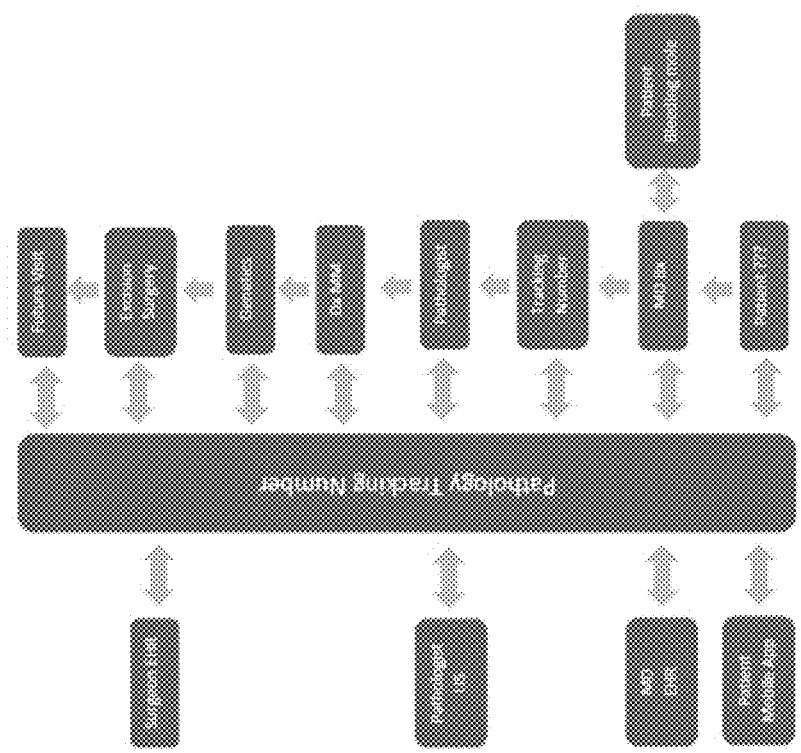
FIG. 7A illustrates an example conceptual view of how the tracking number interrelates physicians and testing, according to some embodiments.

FIG. 7A conceptually illustrates how the medical event tracking number is used in certain embodiments, to track an event throughout a diagnosis and treatment cycle for a patient. The illustrated example shows the diagnosis and excision of a patient's bleeding mole, and involves, in addition to the patient, the physician, pathologist and the surgeon. On the right side of the figure, the patient's mobile app, the physician's EHR system, the pathologist's LIS system, and the surgeon's EHR system are shown. The figure illustrates that they, or more specifically, their respective EHR systems, are all interconnected by the same medical event tracking number (indicated as "pathology tracking number" in the figure).

By enabling the intercommunication on a common communication platform between the physician, pathologist and the surgeon in relation to the particular pathology specimen via the unique medical event tracking number assigned to corresponding tracked event, embodiments allow recommendations from the pathologist and/or a radiologist be recorded in the patient information such that it is accessible to the surgeon and/or the physician. The unique medical event tracking number thus can link the entire care team for the patient and provide for effective coordination of future testing/procedures. Some embodiments may allow future scheduled events or sequence of events to be changed by any of the providers and/or the patient.

The unique medical event tracking number also enables effective sharing of quality metrics.

The unique medical event tracking number implemented in the QAM using data structures 602 and 604, enables changing the time frame for future events, for example, in radiology one may have less than an hour for a pneumothorax to be corrected, or the severity of a melanoma may mean every 3 months vs every 6 months exams, The unique medical event tracking number also allows documentation of event completion, notification of incomplete event closure, allows data to flow to reports retrospectively in some embodiments so that when a PDF report is read "hovering" over embedded tracking number reveals future linked events.

The unique medical event tracking number enables filing data into patient medical records linked to tracking number. For example, report data from the LIS etc. may be sent to the racking number which disseminates information to appropriate EHR system and/or appropriate EHR.

The figure also illustrates the progression of the diagnosis and treatment. To the right of the illustrated "pathology tracking number", starting from the bottom it is shown that the patient visits the physician for the initial diagnosis ("MD Bx") of the bleeding mole. The physician takes a sample, obtains a tracking number, and sends the sample with a label attached with the tracking number to the pathologist. The physician also communicates electronically with the pathologist regarding the sample and the proposed diagnosis. The pathologist completes his diagnosis ("Dx MM") and requires a genetics test ("Genetics") to be performed. Subsequently, the surgeon performs the excision surgery ("Excision surgery"). Finally a future visit is scheduled. The figure illustrates that all of the events of the initial patient visit to the physician, the sample, the pathologist visit, the pathologist diagnosis, the genetics testing, the excision surgery, and the future visit are all trackable by the same medical event tracking number here referred to as the pathology tracking number.

Figure 7B:
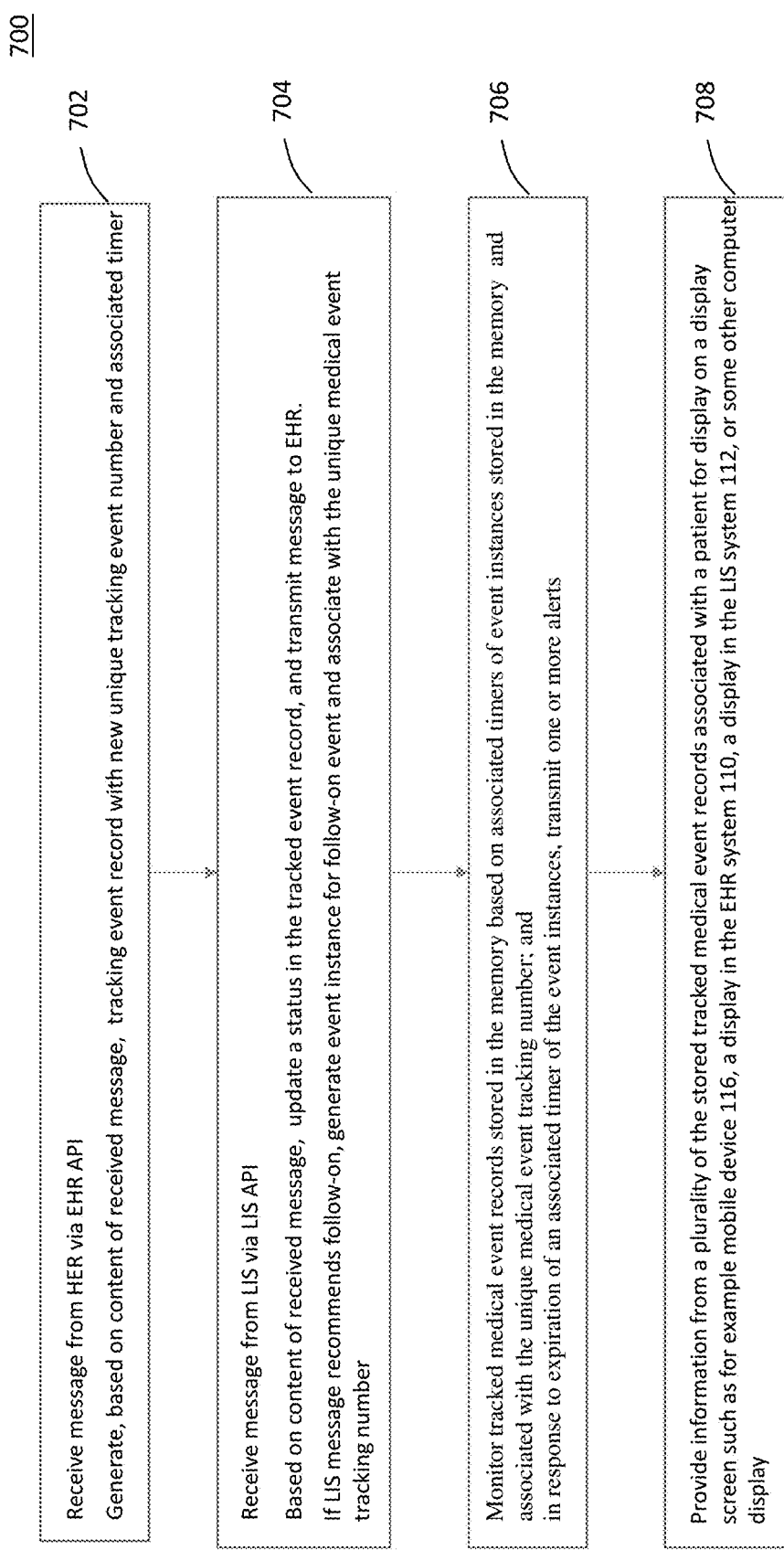
FIG. 7B illustrates a flowchart of a process for tracking and quality assurance of medical events, according to some embodiments.

FIG. 7B illustrates a flowchart for a process 700 for tracking and quality assurance of medical events in accordance with some embodiments. Process 700 may be performed by one or more computers that, via one or more network interfaces, interface to one or more EHR systems and one or more LIS systems. For example, process 700 may be performed by the medical event tracking system 102 described in relation to FIG. 1 and other figures, which provides an API 106 interfacing to one or more EHR systems 110 and another API 108 interfacing to one or more LIS 112. In some embodiments, system 102 may also include mobile device 116 (e.g. used by a patient, medical professional, care provider etc.) and/or analytics system 114.

As an example, process 700 is described in relation to the scenario described in FIG. 2. In the scenario of FIG. 2, when the nurse is ready to generate the label to affix to the specimen one or more messages in a format defined by the interface 106 are exchanged between the EHR system 110 and system 102.

In response to the one or more messages received from the EHR system 110, at operation 702, the system 102 generates a unique medical event tracking number to track the specimen excised or to be excised, generates a corresponding tracked medical event record based on a tracked event record structure 602 and at least one event record based on an event data structure 604 in a memory of system 102. System 102 associates at least one timer of the one or more generated event records with the generated tracked medical event record. An event type and/or event subtype and the associated timer of the generated tracked medical event record and/or the corresponding one or more event records are set in accordance with a code included in the received first type of message. A proposed diagnosis communicated from the EHR system may also be recorded in an event record.

Operation 702 may include generating a label for the specimen including, for example, any of patient demographics, the proposed diagnosis, and the generated unique medical event tracking number or another number associated in the memory of system 102 with the unique medical event tracking number. In some embodiments, the label is formed by generating a machine-readable code.

When the pathologist in the scenario of FIG. 2 renders the diagnosis and recommendation, at operation 704, one or more messages as defined by the interface 108 are exchanged between the system 102 and LIS 112. In response to one or more messages received from LIS 112, the system 102 may update a status of the generated tracked medical event record to indicate that the medical event corresponding to the pathologist diagnosis is complete, and may transmit a status message to the EHR system 110.

Based on the diagnosis and/or recommendations encoded in the one or more messages received from LIS 112, system 102 determines whether one or more follow-on medical events is necessary. Then, for each one or more follow-on medical events determined to be necessary, the system 102 generates a new event instance corresponding to the one or more follow on medical events in the memory of system 102, associates the new event instance with the unique medical event tracking number, and associates a timer with the new event instance. An event type and/or event subtype and an associated timer of the new event instance is set in accordance with a code included in the messages received from LIS 112. In some embodiments, a plurality of new event instances are created in the memory of system 102 in response to the messages received from LIS 112, and each of the generated event instances is associated with the unique medical event tracking number.

In some embodiments, the one or more messages received from the LIS in operation 704 may include a pathologist diagnosis and a recommendation code from a lab. The system 102, using interface 108, imports (e.g., by performing any necessary conversions) the pathologist diagnosis and the recommendation code to the generated tracked medical event record and the corresponding event records. The recommendation code may identify any additional procedures needed and time parameters for completion. For example, in some embodiments, the recommendation code from the LIS identifies additional procedures including at least one of re-testing the patient, expanding a scope of testing, recommending patient follow-up visits, and/or recommending a referral to another specialist. The recommendation code may further identify time parameters for the recommended additional procedures. In some embodiments, the recommendation code may identify additional procedures including at least one of re-excision of a lesion, excision of the lesion with a specific margin of skin, recommending patient follow-up visits, and/or recommending a referral to another specialist.

Operation 704 may include identifying time metrics for follow-up activity based on the one or more messages from the LIS, for example, based on the pathologist diagnosis and the recommendation code. Operation 704 may also include setting a timer associated with an event instance stored in the at least one memory in accordance with identified time metrics, wherein the event instance is associated in the memory of system 102 with the generated tracked medical event record.

When the one or more messages from the LIS includes a recommendation for additional procedures, in response to one of the identified additional procedures, the system 102 may generate a second unique medical event tracking number and a second tracked medical event record, and associate the second tracked medical event record with the first tracked medical event record.

The information relating to the specimen received from the LIS and/or the EHR system may include a date that the specimen was sent to the lab, a location of the lab, arrival date at the lab, arrival date for the pathologist diagnosis at the patient's care provider, date of patient notification of the pathologist diagnosis, additional recommendations or treatments, dates of future procedures, and dates of communications sent to the patient. In some embodiments, the specimen may include an x-ray or other scan.

In some embodiments, the QAM may automatically identify and generate referral recommendations and time metrics, and the corresponding data structures in the memory of the system 102, based on the pathologist recommendation and diagnosis. In some embodiments, the system 102 may store a set of programmable rules and/or algorithms that can automatically add additional medical events, such as, for example, referrals and corresponding time and monitoring parameters associated with the same medical event tracking number or a new medical event tracking number that is linked to an existing medical event tracking number, in response to specifically identified recommendations and/or diagnosis being identified in a message from an EHR system or LIS. For example, in response to receiving a diagnosis of malignant melanoma from the pathologist, the system may automatically add an event for a follow-up in a predefined time interval (according to a default rule based on the diagnosis) and also a new tracked event, with a new unique medical event tracking number that is linked to the tracking number associated with the received diagnosis, for a re-excision. The system may also automatically update any living documents in which the tracking number associated with the received diagnosis is embedded to include the newly received information.

In some embodiments, with respect to operations 702 and 704, when EHR system 110 and/or LIS system 112 transmits messages to the respective interface 106 and/or 108 using a coding system that is proprietary or different from the coding system used by the system 102, such as ICD-10 coding described above, conversions between those proprietary or different codes and the codes of the system 102 may be performed at the interfaces 106 and/or 108. For example, conversion from a first code in the messages received from an EHR system at the interface 106 to an event type and/or subtype stored in the memory of system 102 in association with a tracked medical event record, and/or conversion from the stored event type and/or event subtype into a second code used in an LIS for messages to/from the LIS may be performed at the interface 108.

The recommendation code used by the system 102 may include default coding sequences that reflect individual physician, practice group, medical society and national preferences.

The system 102, in a continuing operation 706, monitors the tracked medical event records stored in the memory based on respective associated timers of event instances stored in the memory and associated with the respective medical event records. In response to expiration of an associated timer of the event instances, the system 102 may transmit one or more alerts and/or may perform other operations.

Operation 706 may include monitoring the follow-up activity and corresponding time metrics, and automatically sending alerts (e.g. text messages, emails, automated phone call, automated mailings etc.) when the follow-up activity does not take place according to the time metrics. Operation 706 may also include, when the patient, care provider, or lab does not respond to a communication within a preset time period, generating a closed diagnosis letter or message to that entity.

The system 102, in a continuing operation 708, provides information from a plurality of the stored tracked medical event records associated with a patient for display on a display screen such as for example mobile device 116, a display in the EHR system 110, a display in the LIS system 112, or some other computer display. Some example displays are described in relation to FIG. 10. According to some embodiments, in the display, medical events corresponding to the plurality of tracked medical event records are arranged in a first area of the display screen, a first tracked medical event record from the plurality of stored tracked medical event records is associated with a plurality of event instances stored in the memory of system 102, and the plurality of event instances are represented in a second area of the display screen.

In some embodiments, medical events corresponding to the plurality of tracked medical event records are arranged on the display screen, a first area of the display screen displaying past and future medical events associated with a current medical event for the patient and a second area of the display screen displaying one or more other related medical events. In some embodiments, medical events corresponding to the plurality of tracked medical event records are arranged in a first area of the display screen as a tree.

Operation 708 may include the system 102 communicating information relating to any specimen and a status of the diagnosis from any medical professional to the patient. For example, the patient may access the system 102 using a mobile device 116 and a web application. In some embodiments, system 102 may allow a patient and/or other authorized person to make changes to the records stored in the memory of system 102, for example, to make change to the time settings, referral events and the like.

Figure 8:
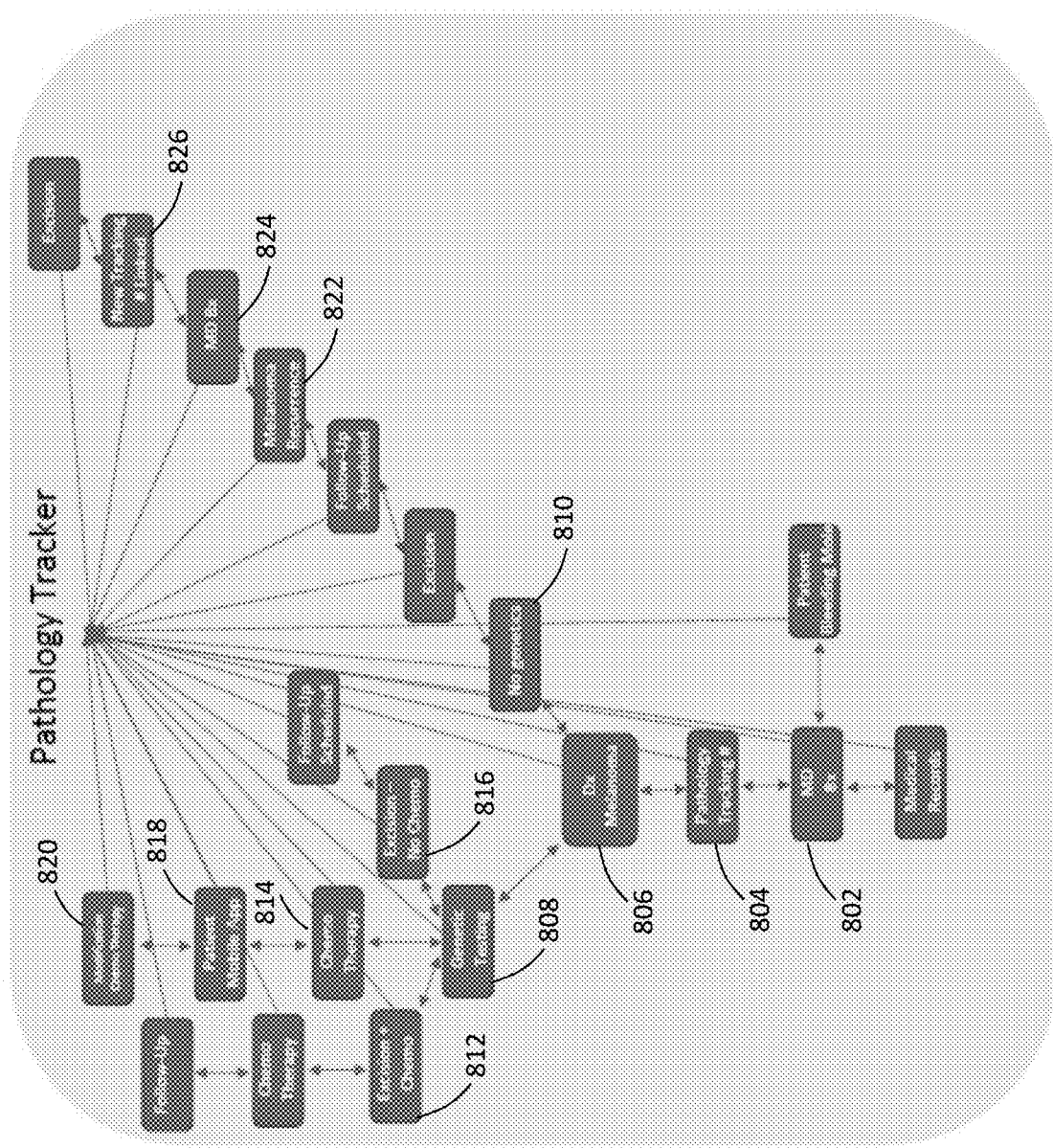
FIG. 8 illustrates an example conceptual view of how the tracking number interrelates physicians and testing, according to some embodiments.

FIG. 8 illustrates another conceptual view of the tracking number associating multiple treatment plans for a particular patient's bleeding mole. Based on the physician's initial diagnosis and sampling at 802 of the patient's bleeding mole, a tracking number is generated at 804 for the pathology sample, and the pathologist determines at 806 a diagnosis of melanoma.

Based on the diagnosis at 806, a treatment path including genetic testing 808 or a path including no genetic testing 810 may be taken. When the genetic testing path 808 is taken, based on the genetic test, one of three paths—a path with excision and chemotherapy 812, a path with chemotherapy and no excision 814 and a path with excision and no chemotherapy 816—may be taken.

The path of 814 illustrates the patient's mobile app introducing a medical event 818 to modify chemotherapy 820.

The path of no genetic testing 810 illustrates a recurrence of the melanoma being detected at 822 in relation to a follow-up visit, and causing a new pathology sample to be taken at 824 (with a new corresponding tracking number being generated 826) for the recurrent melanoma.

Figure 9A:
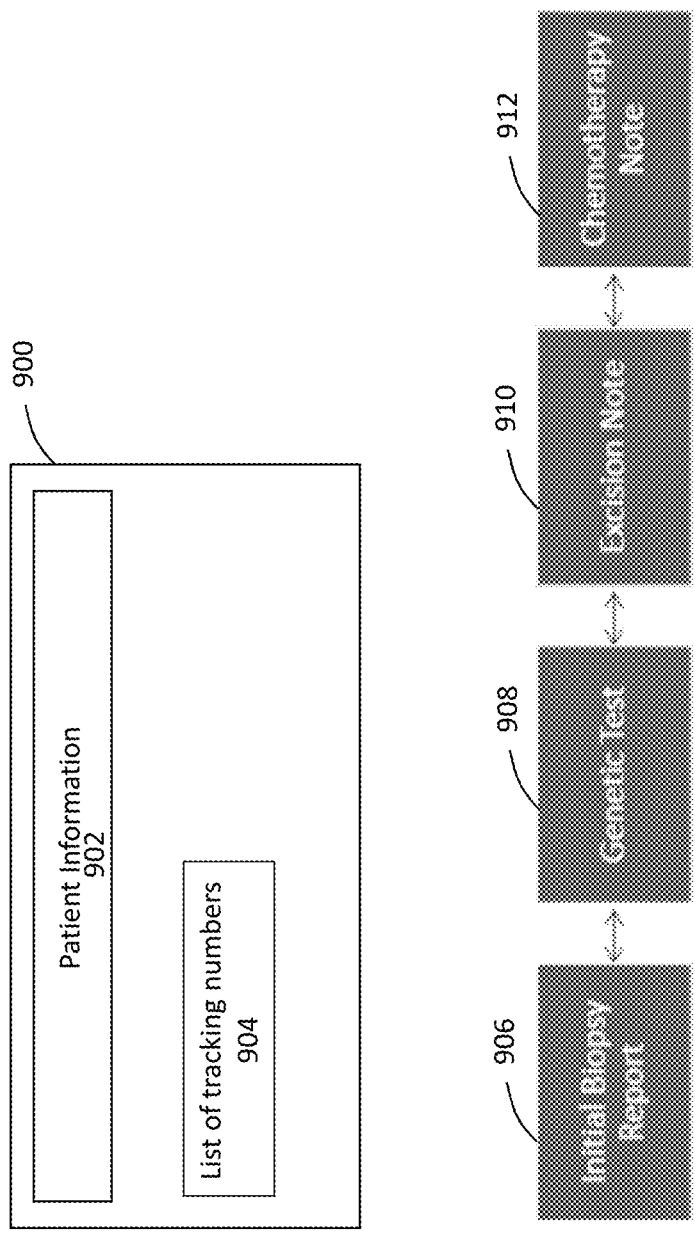
FIG. 9A schematically illustrates an example living portable document format document, according to some example embodiments.

FIG. 9A conceptually illustrates a living document 900, according to certain example embodiments. According to EHR, the patient medical record is provided in a format referred to as the "portable document format" (PDF). For example, the living document may be a pathology report PDF.

The living document 900 includes patient information 902 which identifies the patient. Additionally, according to some embodiments, one or more medical event tracking numbers are embedded in the living document. The figure shows a list 904 of embedded medical event tracking numbers. In some embodiments, each of the tracking numbers pertain to a diagnosis and/or treatment plan. In some embodiments, for example, each embedded tracking number may pertain to a respective pathology specimen of the patient.

The living document 900 may be dynamically updated to include the data of each event as each event pertaining to a particular tracking number is completed. All future linked data is sent and/or integrated "retro-actively" to each report along the chain of events associated with the tracking number. As described in relation to the data structures 602 and 604 above, information of the respective related events can be accessed from a particular event by following the pointers from that event's data structure 602 and/or 604.

According to an embodiment, the living PDF 900 is dynamically updated to include details of all the completed events pertaining to each of the tracking numbers in the list 904. The dynamically included details may be arranged in separate areas for the respective tracking numbers.

In some embodiments, when a user "hovers" over the report (e.g., position mouse cursor or touch over display area of the report), future and/or past events pertaining to the event hovered over is shown. In this manner, it is ensured that the viewer is always looking at the event relative to other events associated with the same tracking number. For example, if the initial biopsy 906 and the genetic test 908 have already been completed when the viewer attempts to view the living document 900, the information regarding them will already have been dynamically included in the living document 900. When the viewer, hovers over the display area of the genetic test report 908 in the document 900, future events 910 and 912 are displayed with a selection of information about each.

This may improve the efficiency of the care team by preventing "chart flipping" (i.e., where the care provider has to separately open and view multiple files to obtain the information regarding the full diagnosis and treatment associated with a particular pathology specimen) or having to search through the entire chart to see what happened.

Figure 9B:
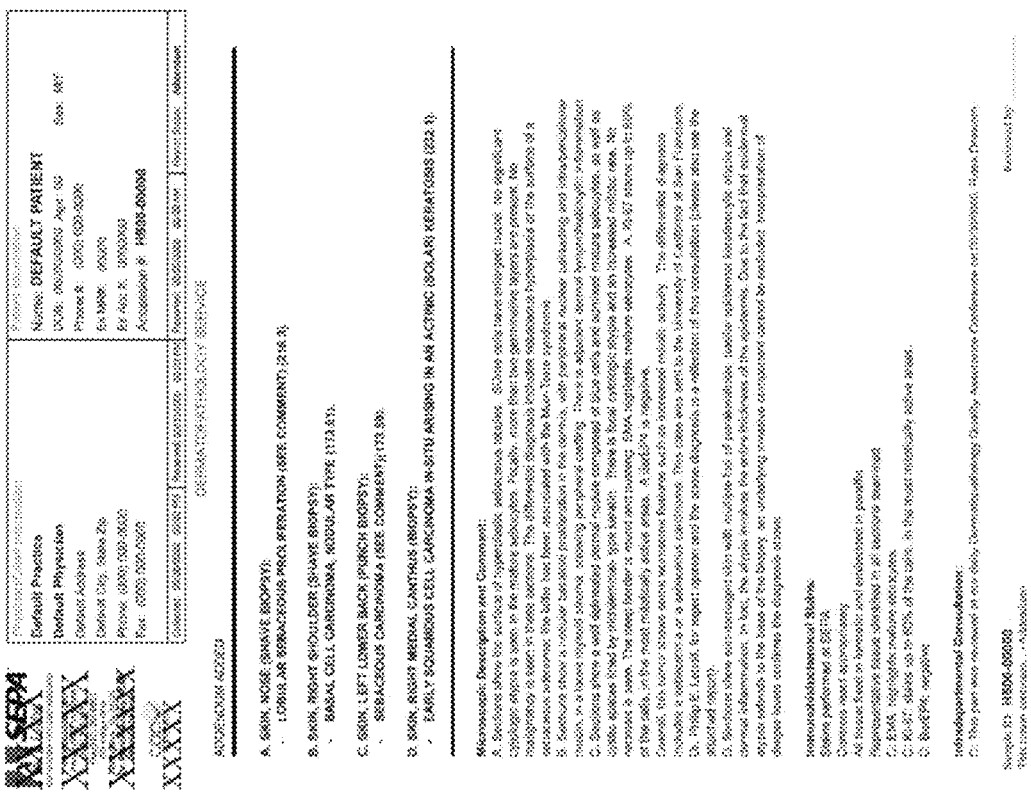
Figure 9C:
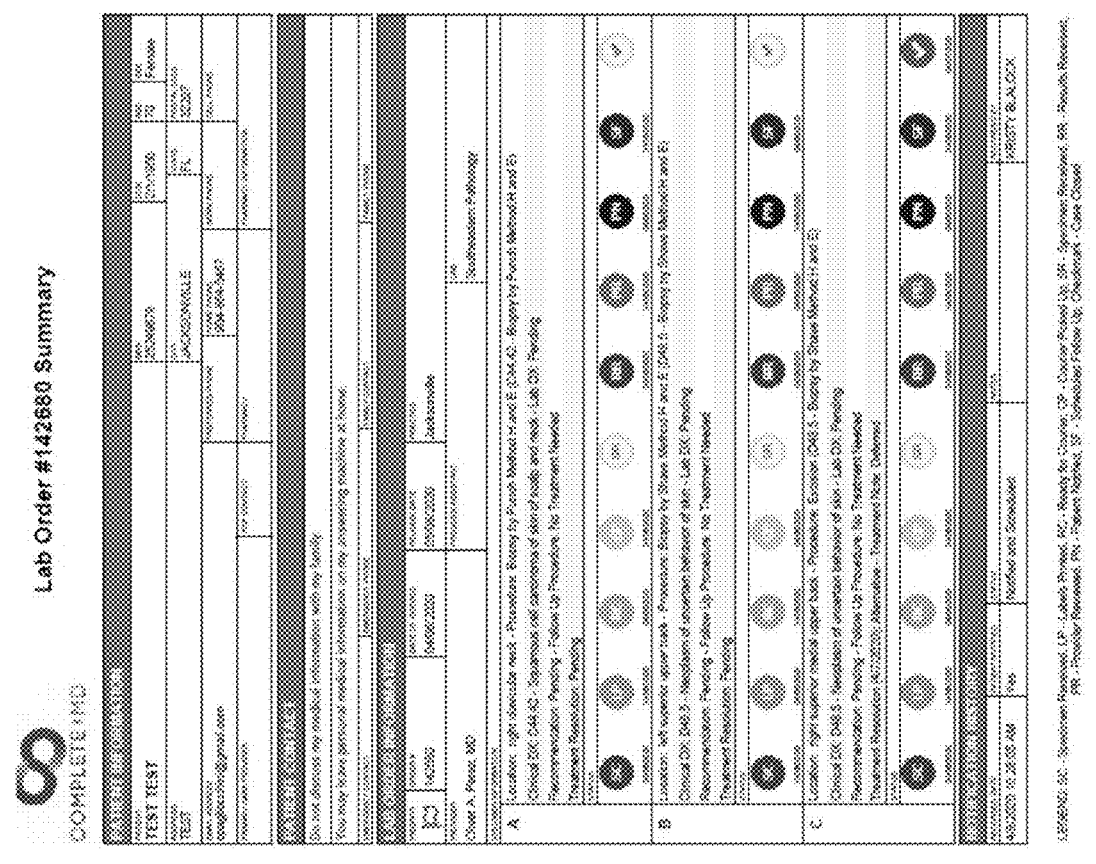

FIGS. 9B and 9C show other examples of living PDF documents, according to some embodiments. FIG. 9B shows a dermopathology report for a particular patient, having information about four separate biopsies (indicated as A, B, A and D) dynamically incorporated into the single document with the appropriate information from each biopsy and diagnosis being incorporated into the appropriate respective sections in the report. After having embedded the four tracking numbers for biopsies A, B, C and D in the report, the system 102 dynamically updates the report at runtime whenever the report is displayed and/or printed to include the information and results from the all the events completed so far in relation to each of the tracked events. In this manner a care provider or patient accessing a specified link to the document, is automatically served the most current information regarding each of the tracked events by the system traversing the tracked event and/or event chains for each of the tracked events embedded in the document accessed by the link.

FIG. 9C shows another example of a living PDF document in form of a lab order summary for a particular patient. Three tracked events (indicated as A, B and C) are embedded in the document, and for each of the tracked events, all events are shown with the current status (SC, LP, RC, CP, etc.). When the user hovers over ant of the tracked events or other events, any future or past event associated with the tracked event or other event may be shown.

The ability to show all information associated with a particular tracked event, including events directly linked to that tracked event and/or other tracked events that are linked to the particular tracked event, enables a care provider, patient or other authorized entity to view all of the information related to a particular set of tracked events regardless of the passing of time between events or the number of intervening events between two tracked or other events.

Figure 10:
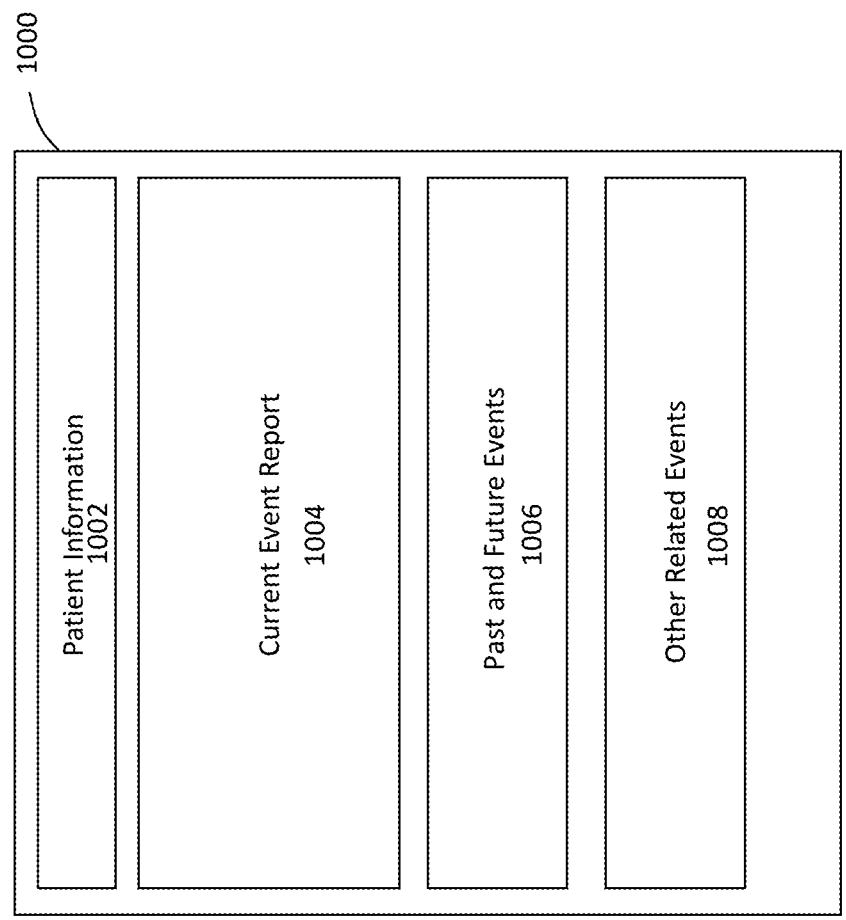
FIG. 10 schematically illustrates an display view, according to some embodiments.

FIG. 10 schematically illustrates a display view 1000 that may be provided to the patient, medical professional and/or insurance professional, according to some embodiments. For example, the display view 1000 may be rendered on a patient's mobile device, or a physician's display. The view may have separate areas for patient information (e.g. personally identifiable information, demographic information) 1002, displaying details of a selected medical event 1004, an area for displaying a scrollable list of medical events associated with the currently selected tracking number 1006, and an area for displaying other associated tracking numbers or other medical events 1008.

According to an embodiment, the display view 1000 enables viewing the living PDF document described in relation to FIG. 9 above. For example, at a particular instant, the viewer may be viewing the details of the genetics test report 908 resulting from a tracked event corresponding one of the embedded tracking numbers. Then, the details of the genetics test report 908 is displayed in display area 1004, and a scrollable list of past and future events associated with the report 908 (e.g. past event report 906 and future event reports 910 and 912) are indicated in display area 1006.

FIG. 11 generally illustrates a computer system 201 suitable for use as the client and server components of the described system. It will be appreciated that the client and server computers will run appropriate software and that the client and server computers may be somewhat differently configured with respect to the processing power of their respective processors and with respect to the amount of memory used. Computer system 201 includes a processing system (e.g. one or more processors) 203 and a system memory 205. A system bus 207 couples various system components including system memory 205 to processing system 203. System bus 207 may be any of several types of bus structures including a memory bus or memory controller, a peripheral bus, and a local bus using any of a variety of bus architectures. System memory 205 includes read only memory (ROM) 252 and random access memory (RAM) 254. A basic input/output system (BIOS) 256, containing the basic routines that help to transfer information between elements within computer system 201, such as during start-up, is stored in ROM 252. Computer system 201 further includes various drives and associated computer-readable media. A hard disk drive 209 reads from and writes to a (typically fixed) magnetic hard disk 211; a magnetic disk drive 213 reads from and writes to a removable "floppy" or other magnetic disk 215; and an optical disk drive 217 reads from and, in some configurations, writes to a removable optical disk 219 such as a CD ROM or other optical media. Hard disk drive 209, magnetic disk drive 213, and optical disk drive 217 are connected to system bus 207 by a hard disk drive interface 221, a magnetic disk drive interface 223, and an optical drive interface 225, respectively. The drives and their associated computer-readable media provide nonvolatile storage of computer-readable instructions, SQL-based procedures, data structures, program modules, and other data for computer system 201. In other configurations, other types of computer-readable media that can store data that is accessible by a computer (e.g., magnetic cassettes, flash memory cards, digital video disks, Bernoulli cartridges, random access memories (RAMs), read only memories (ROMs) and the like) may also be used.

A number of program modules may be stored on the hard disk 211, removable magnetic disk 215, optical disk 219 and/or ROM 252 and/or RAM 254 of the system memory 205. Such program modules may include an operating system providing graphics and sound APIs, one or more application programs, other program modules, and program data. A user may enter commands and information into computer system 201 through input devices such as a keyboard 227 and a pointing device 229. Other input devices may include a microphone, joystick, game controller, satellite dish, scanner, or the like. These and other input devices are often connected to the processing unit 203 through a serial port interface 231 that is coupled to the system bus 207, but may be connected by other interfaces, such as a parallel port interface or a universal serial bus (USB). A monitor 233 or other type of display device is also connected to system bus 207 via an interface, such as a video adapter 235.

The computer system 201 may also include a modem or broadband or wireless adapter 237 or other means for establishing communications over the wide area network 239, such as the Internet. The modem 237, which may be internal or external, is connected to the system bus 207 via the serial port interface 231. A network interface 241 may also be provided for allowing the computer system 201 to communicate with a remote computing device 250 via a local area network 258 (or such communication may be via the wide area network 239 or other communications path such as dial-up or other communications means). The computer system 201 will typically include other peripheral output devices, such as printers and other standard peripheral devices.

As will be understood by those familiar with web-based forms and screens, users may make menu selections by pointing-and-clicking using a mouse, trackball or other pointing device, or by using the TAB and ENTER keys on a keyboard. For example, menu selections may be highlighted by positioning the cursor on the selections using a mouse or by using the TAB key. The mouse may be left-clicked to select the selection or the ENTER key may be pressed. Other selection mechanisms including voice-recognition systems, touch-sensitive screens, etc. may be used, and the invention is not limited in this respect.

The embodiments improve the performance of the present computerized diagnosis and treatment process by providing a quality assurance module that interfaces to EHR systems in the medical service providers and to lab information systems. In contrast to the tracking of medical events based on patient name or the like, the quality assurance module enables tracking patients based on respective medical events. The capability to track medical events enables the improving of the accuracy and completion of diagnostic and treatment plans. The quality assurance module, in some embodiments, integrates to EHR systems and lab information systems by well-defined API such that it enables the integration of numerous EHR systems and lab information systems. In some embodiments, the quality assurance module employs a two-level record structure to facilitate efficiently updating EHR systems etc., with the relevant tracked event information. The two-level records and associated data structures in some embodiments also facilitate the tracking of tracked events and other events in order to ensure the completion of diagnosis and treatment plans.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A medical event tracking computer system, comprising:
at least one memory configured to store a plurality of tracked medical event records, each tracked medical event record including a unique medical event tracking number and corresponding to a tracked medical event in relation to a patient;
at least one network communication interface; and
a processing system comprising at least one processor, the processing system being configured to:

provide, via the at least one network communication interface, a first application programming interface to a patient information system and a second application programming interface to a medical testing information system, wherein the first application programming interface and the second application programming interface are configured to convert between medical event codes encoded in one or more non-standard medical event coding schemes and medical event codes encoded in a standard medical event coding scheme;
receive a first type of message from the patient information system via the first application programming interface, the first type of message being generated in the patient information system in response to a first user of the patient information system indicating, on a display device, an excision region for the patient;
in response to the first type of message: (1) generate a unique medical event tracking number, (2) generate a corresponding tracked medical event record in the at least one memory, and (3) associate at least one first timer with the generated tracked medical event record, wherein an event type and/or event subtype and the associated first timer of the generated tracked medical event record is set in accordance with a code included in the received first type of message;
communicate the generated unique medical event tracking number to the patient information system and subsequently in response to receiving a further first type of message from the patient information system indicating an excised sample from the region being sent to a laboratory, update the tracked medical event record and the associated at least one first timer;
receive a second type of message from the medical testing information system via the second application programming interface, the second type of message indicating a result of a test of the excised sample provided by a user of the medical testing system;
in response to the second type of message: (1) convert, in the second type of message, medical event codes encoded in a first one of the one or more non-standard medical event coding scheme; (2) further update a status of the tracked medical event record in the at least one memory, medical event codes in the tracked medical event record in the at least one memory being encoded in the standard medical event coding scheme and comprising the converted corresponding medical event codes, and transmit a status message to the patient information system so that the patient information system is informed of a current status of the tracked medical event record in real-time;
in further response to the second type of message from the medical testing information system received via the second application programming interface, based on a content including the converted corresponding medical event codes of the received second type of message and based on the result of the test of the excised sample, determine whether a follow-on excision of a second excision region for the patient is necessary and for the follow-on excision determined to be necessary: (1) generate a new event instance corresponding to the follow-on excision of the second region in the at least one memory, (2) associate the new event instance with the unique medical event tracking number, and update the tracked medical event record in the least one memory to include the new event instance, (3) associate a second timer with the new event instance, wherein an event type and/or event subtype and the associated second timer of the new event instance is set in accordance with a code included in the converted corresponding medical event codes and/or the received first type of message, and (4) monitor, based on the second timer, a staus of the follow-on excision and automatically, based on the monitored status, transmit one or more alerts so that one or more of the patient information system, the medical testing information system, and the patient are informed of a current status of the follow-on excision in real-time; and transmit one or more messages including information associated with the generated tracked medical event record to a requester.

2. The medical event tracking computer system according to claim 1, wherein the processing system is further configured to generate a plurality of new event instances in response to receiving the second type of message and associate each of the generated event instances with the unique medical event tracking number.

3. The medical event tracking computer system according to claim 1, wherein the processing system is further configured to:

monitor the tracked medical event record stored in the at least one memory based on respective associated timers of event instances stored in the at least one memory and associated with the unique medical event tracking number; and in response to expiration of an associated timer of the event instances, transmit one or more alerts.

4. The medical event tracking computer system according to claim 1, wherein the processing system is further configured to:

provide for display, on a display screen, of information from a plurality of the stored tracked medical event records associated with a patient, wherein medical events corresponding to the plurality of tracked medical event records are arranged in a first area of the display screen, wherein a first tracked medical event record from the plurality of stored tracked medical event records is associated with a plurality of event instances stored in the at least one memory, and wherein the plurality of event instances are represented in a second area of the display screen.

5. The medical event tracking computer system according to claim 1, wherein the processing system is further configured to:

provide from the at least one memory, for display on a display screen, information from a plurality of the stored tracked medical event records associated with a patient, wherein medical events corresponding to the plurality of tracked medical event records are arranged on the display screen, a first area of the display screen displaying past and future medical events associated with a current medical event for the patient and a second area of the display screen displaying one or more other related medical events.

6. The medical event tracking computer system according to claim 1, wherein the processing system is further configured to:

provide for display, on a display screen, of information from a plurality of tracked medical event records associated with a patient, wherein medical events corresponding to the plurality of tracked medical event records are arranged in a first area of the display screen as a tree.

7. The medical event tracking computer system according to claim 1, wherein the processing system is further configured to:

convert from a first code in the first type of message in the first application programming interface to an event type and/or subtype stored in the at least one memory in association with a tracked medical event record; and convert from the stored event type and event subtype into a second code in the second application programming interface.

8. The medical event tracking computer system according to claim 1, wherein the processing system is further configured to:

provide an interface to an analytics system to access information associated with the stored tracked medical event records.

9. The medical event tracking computer system according to claim 1, wherein the processing system is further configured to:

provide an interface to a mobile device, the provided interface enabling entry of data for storing in the at least one memory in association with a tracked medical event record.

10. The medical event tracking computer system according to claim 1, wherein the stored plurality of medical event records are devoid of personally-identifiable information data of patient.

11. The medical event tracking computer system according to claim 1, wherein the processing system is further configured to:

in response to messages received from the first interface or the second interface, retro- actively update one or more stored patient information documents associated with the generated unique medical event tracking number.

12. The medical event tracking computer system according to claim 1, wherein the processing system is further configured to:

(a) generate a label for a specimen including patient demographics, a proposed diagnosis, and the generated unique medical event tracking number or another number associated in the at least one memory with the unique medical event tracking number;

(b) encode at least the proposed diagnosis in the generated tracked medical event record;

(c) receive, in the second type of message, a pathologist diagnosis and a recommendation code from a lab and importing the pathologist diagnosis and the recommendation code to the generated tracked medical event record, wherein the recommendation code identifies any additional procedures needed and time parameters for completion;

(d) identify time metrics for follow-up activity based on the pathologist diagnosis and the recommendation code; and (e) set a timer associated with an event instance stored in the at least one memory in accordance with the identified time metrics, wherein the event instance is associated in the at least one memory with the generated tracked medical event record.

13. The medical event tracking computer system according to claim 12, wherein step (a) is practiced by generating a machine-readable code.

14. The medical event tracking computer system according to claim 13, wherein the recommendation code in step (c) identifies additional procedures including at least one of re- testing the patient, expanding a scope of testing, recommending patient follow-up visits, and recommending a referral to another specialist.

15. The medical event tracking computer system according to claim 14, wherein the recommendation code in step (c) further identifies the time parameters for the recommended additional procedures.

16. The medical event tracking computer system according to claim 12, wherein the proposed diagnosis is a melanoma, and wherein the recommendation code in step (c) identifies additional procedures including at least one of re-excision of a lesion, excision of the lesion with a specific margin of skin, recommending patient follow-up visits, and recommending a referral to another specialist.

17. The medical event tracking computer system according to claim 16, wherein the processing system is further configured to:
  in response to one of the identified additional procedures, generate a second unique medical event tracking number and a second tracked medical event record; and
  associate the second tracked medical event record with the first tracked medical event record.

18. The medical event tracking computer system according to claim 12, further comprising:
  (e) monitoring the follow-up activity and corresponding time metrics; and
  (f) automatically sending alerts when the follow-up activity does not take place according to the time metrics.

19. The medical event tracking computer system according to claim 18, further comprising, wherein when the patient does not respond to the email communication within a preset time period, generating a closed diagnosis letter to the patient.

20. The medical event tracking computer system according to claim 12, wherein the quality assurance module communicates information relating to the specimen and a status of the pathologist diagnosis to the patient.

21. The medical event tracking computer system according to claim 20,
  wherein the information relating to the specimen comprises a date that the specimen was sent to the lab, a location of the lab, arrival date at the lab, arrival date for the pathologist diagnosis at the patient's care provider, date of patient notification of the pathologist diagnosis, additional recommendations or treatments, dates of future procedures, and dates of communications sent to the patient.

22. The medical event tracking computer system according to claim 12, wherein the specimen comprises an x-ray.

23. The medical event tracking computer system according to claim 12, further comprising automatically identifying with the quality assurance module referral recommendations and time metrics.

24. The medical event tracking computer system according to claim 12, wherein the recommendation code comprises default coding sequences that reflect individual physician, practice group, medical society and national preferences.

25. A medical event tracking method, comprising:
  providing, via at least one network communication interface, a first application programming interface to a patient information system and a second application programming interface to a medical testing information system, wherein the first application programming interface and the second application programming interface are configured to convert between medical event codes encoded in one or more non-standard medical event coding schemes and medical event codes encoded in a standard medical event coding scheme;
  receiving a first type of message from the patient information system via the first application programming interface, the first type of message being generated in the patient information system in response to a first user of the patient information system indicating, on a display device, an excision region for the patient;
  in response to the first type of message received: (1) generating a unique medical event tracking number, (2) generating a corresponding tracked medical event record in the at least one memory, and (3) associating at least one first timer with the generated tracked medical event record, wherein an event type and/or event subtype and the associated first timer of the generated tracked medical event record is set in accordance with a code included in the received first type of message;
  communicating the generated unique medical event tracking number to the patient information system and subsequently in response to receiving a further first type of message from the patient information system indicating an excised sample from the region being sent to a laboratory, update the tracked medical event record and the associated at least one first timer;
  receiving a second type of message from the medical testing information system via the second application programming interface, the second type of message indicating a result of a test of the excised sample provided by a user of the medical testing system;
  in response to a second type of message received from the medical testing information system via the second application programming interface: (1) converting, in the second type of message, medical event codes encoded in a first one of the one or more non-standard medical event coding schemel (2) updating a status of the tracked medical event record in the at least one memory, medical event codes in the tracked medical event record in the at least one memory being encoded in the standard medical event coding scheme and comprising the converted corresponding medical event codes, and (3) transmitting a status message to the patient information system so that the patient information system is informed of a current status of the tracked medical event record in real-time;
  in further response to the second type of message from the medical testing information system received via the second application programming interface, based on a content including the converted corresponding medical event codes of the received second type of message and based on the result of the test of the excised sample, determine whether a follow-on excision of a second excision region for the patient is necessary and for the follow-on excision determined to be necessary: (1) generate a new event instance corresponding to the follow-on excision of the second region in the at least one memory, (2) associate the new event instance with the unique medical event tracking number and update the tracked meical event record in the at least one memory to include the new event instance, (3) associate a second timer with the new event instance, wherein an event type and/or event subtype and the associated second timer of the new event instance is set in accordance with a code included the converted corresponding medical event codes and/or the received first type of message, and (4) monitor, based on the second timer, a status of the follow-on excision and automatically, based on the monitored status, transmit one or more alerts so that one or more of the patient information system, the medical testing information system, and the patient are informed of a current status of the follow-on excision in real-time; and transmitting one or more messages including information associated with the generated tracked medical event record to a requester.

26. A non-transitory computer readable storage medium storing instructions for medical event tracking, the instructions, when executed by a processing system including one or more processors, causes the processing system to perform operations comprising:

providing, via at least one network communication interface, a first application programming interface to a patient information system and a second application programming interface to a medical testing information system;

receiving a first type of message from the patient information system via the first application programming interface, the first type of message being generated in the patient information system in response to a first user of the patient information system indicating, on a display device, an excision region for the patient;

in response to the first type of message received: (1) generating a unique medical event tracking number, (2) generating a corresponding tracked medical event record in the at least one memory, and (3) associating at least one first timer with the generated tracked medical event record, wherein an event type and/or event subtype and the associated first timer of the generated tracked medical event record is set in accordance with a code included in the received first type of message;

communicating the generated unique medical event tracking number to the patient information system and subsequently in response to receiving a further first type of message from the patient information system indicating an excised sample from the region being sent to a laboratory, update the tracked medical event record and the associated at least one timer;

receiving a second type of message from the medical testing information system via the second application programming interface, the second type of message indicating a result of a test of the excised sample provided by a user of the medical testing system;

in response to the second type of message: (1) convert, in the second type of message, medical event codes encoded in a first one of the one or more non-standard medical event coding schemes to corresponding medical event codes encoded in the standard medical event coding scheme; (2) further updating a status of the generated tracked medical event record in the at least one memory, medical event codes in the tracked medical event record in the at least one memory being encoded in the standard medical event coding scheme and comprising the converted corresponding medical event codes; and (3) transmitting a status message to the patient information system so that the patient information system is informed of a current status of the tracked medical event record in real-time;

in further response to the second type of message from the medical testing information system received via the second application programming interface, based on a content including the converted corresponding medical event codes of the received second type of message and based on the result of the test of the excised sample, determine whether a follow-on excision of a second excision region for the patient is necessary and for the follow-on excision determined to be necessary: (1) generate a new event instance corresponding to the follow-on excision of the second region in the at least one memory, (2) associate the new event instance with the unique medical event tracking number and update the tracked medical event record in the at least one memory to include the new event instance, (3) associate a second timer with the new event instance, wherein an event type and/or event subtype and the associated second timer of the new event instance is set in accordance with a code included in the converted corresponding medical event code and/or the received first type of message, and (4) monitor, based on the second timer, a status of the follow-on excision and automatically, based on the monitored status, transmit one or more alerts so that one or more of the patient information system, the medical testing information system, and the patient are informed of a current status of the follow-on excision in real-time; and transmitting one or more messages including information associated with the generated tracked medical event record to a requester.

* * * * *